US007368428B2

(12) United States Patent
Serrero

(10) Patent No.: US 7,368,428 B2
(45) Date of Patent: May 6, 2008

(54) COMPOSITIONS AND METHODS FOR RESTORING SENSITIVITY OF TUMOR CELLS TO ANTITUMOR THERAPY AND INDUCING APOPTOSIS

(75) Inventor: Ginette Serrero, Ellicott City, MD (US)

(73) Assignee: A&G Pharmaceutical, Inc., Columbia, MD (US)

( * ) Notice: Subject to any disclaimer, the term of this patent is extended or adjusted under 35 U.S.C. 154(b) by 394 days.

(21) Appl. No.: 10/873,484

(22) Filed: Jun. 23, 2004

(65) Prior Publication Data
US 2005/0042225 A1 Feb. 24, 2005

Related U.S. Application Data

(60) Provisional application No. 60/480,439, filed on Jun. 23, 2003.

(51) Int. Cl.
*A61K 39/395* (2006.01)
(52) U.S. Cl. ............. 514/12; 424/130.1; 424/138.1; 424/155.1; 424/156.1
(58) Field of Classification Search ............ 424/130.1, 424/138.1, 141.1, 142.1, 155.1, 156.1
See application file for complete search history.

(56) References Cited

U.S. PATENT DOCUMENTS

| | | | |
|---|---|---|---|
| 5,416,192 A | 5/1995 | Shoyab et al. | |
| 5,725,856 A | 3/1998 | Hudziak et al. | |
| 6,309,826 B1 | 10/2001 | Serrero | |
| 6,511,986 B2 | 1/2003 | Zhang et al. | |
| 6,558,668 B2 | 5/2003 | Liau | |
| 6,570,002 B1 | 5/2003 | Hardwick et al. | |
| 6,586,395 B1 | 7/2003 | Kiefer et al. | |
| 2002/0025543 A1* | 2/2002 | Serrero | 435/7.23 |
| 2005/0175616 A1* | 8/2005 | Kiener et al. | 424/155.1 |

FOREIGN PATENT DOCUMENTS

WO    WO 91 15510 A    10/1991

OTHER PUBLICATIONS

Lu et al. Biochem. Biophys, Research Comm. 1999; 256: 204-207.*
Markert et al. Physiol Genomics 2001; 5: 21-33.*
Wang et al. Clinical Cancer Research 2003; 9: 2221.*
Tockman et al (Cancer Res., 1992, 52:2711s-2718s).*
Slamon et al. (Science vol. 235, Jan. 1987, pp. 177-182).*
International Search Report dated Aug. 31, 2005.
Serrero, G. et al., *Effect of Testosterone on the Growth Properties and on Epidermal Growth Factor Receptor Expression in the Teratoma-derived Tumorigenic Cell Line 1246-3A*, Cancer Research 52, 1992, pp. 4242-4247.
Alberts, B., et al., *Molecular Biology of the Cell*, Garland Publishing, Inc., 1983.
Cross, M. et al., *Growth Factors in Development, Transformation, and Tumorigenesis*, Cell, vol. 64, 1991, pp. 271-280.
Sporn, M.B. et al., *Autocrine Secretion and Malignant Transformation of Cells*, The New England Journal of Medicine, vol. 303, 1980, pp. 878-880.
Zhou, J. et al., *Purification of an Autocrine Growth Factor Homologous with Mouse Epithelin Precursor from a Highly Tumorigenic Cell Line*, The Journal of Biological Chemistry, vol. 268, No. 15, 1993, pp. 10863-10869.
Plowman, G. et al., *The Epithelin Precursor Encodes Two Proteins with Opposing Activities on Epithelial Cell Growth*, The Journal of Biological Chemistry, vol. 267, No. 18, 1992, pp. 13073-13078.
Bateman, A. et al., *Granulins, a Novel Class of Peptide from Leukocytes*, Biochemical and Biophysical Research Communications, vol. 173, No. 3, 1990, pp. 1161-1168.
Nestor, J. et al., *A Synthetic Fragment of Rat Transforming Growth Factor with Receptor Binding and Antigenic Properties*, Biochemical and Biophysical Research Communications, vol. 129, No. 1, 1985, pp. 226-232.
Adelman, J. et al., *In Vitro Deletional Mutagenesis for Bacterial Production of the 20,000-Dalton Form of Human Pituitary Growth Hormone*, DNA, vol. 2, No. 3, 1983, pp. 183-193.
Serrero, G. et al., *An In Vitro Model to Study Adipose Differentiation in Serum-Free Medium*, Analytical Biochemistry 120, 1982, pp. 351-359.
Serrero-Dave, G., *Study of a Teratoma-Derived Adipogenic Cell Line 1246 and Isolation of an Insulin-Independent Variant in Serum-Free Medium*, Cancer Center, University of California, pp. 366-376, 1996.
Serrero, G., *Tumorigenicity Associated with Loss of Differentiation and of Response to Insulin in the Adipogenic Cell Line 1246*, In Vitro Cellular & Developmental Biology, vol. 21, No. 9, 1985, pp. 537-540.
Serrero, G. et al., *Decreased Transforming Growth Factor-β Response and Binding in Insulin-independent Teratoma-Derived Cell Lines with Increased Tumorigenic Properties*, Journal of Cellular Physiology, 149, 1991, pp. 503-511.
Arteaga, C. et al., *Growth Inhibition of Human Breast Cancer Cells in Vitro with an Antibody against the Type I Somatomedin Receptor*, Cancer Research 49, 1989, pp. 6237-6241.
Schofield, P. et al., *The Biological Effects of a High Molecular Weight Form of IGF II in a Pluripotential Human Teratocarcinoma Cell Line*, Anticancer Research 14, 1994, pp. 533-538.
Trojan, J. et al., *Gene therapy of murine teratocarcinoma: Separate functions for insulin-like growth factors I and II in immunogenicity and differentiation*, Proc. Natl. Acad. Sci. USA, vol. 91, 1994, pp. 6088-6092.
Trojan, J. et al., *Treatment and Prevention of Rat Glioblastoma by Immunogenic C6 Cells Expressing Antisense Insulin-Like Growth Factor I RNA*, Science, vol. 259, 1993, pp. 94-96.

(Continued)

*Primary Examiner*—Brandon Fetterolf
(74) *Attorney, Agent, or Firm*—Dickstein Shapiro LLP

(57) ABSTRACT

Methods and compositions for restoring sensitivity to the antitumorigenic effects of antiestrogen therapy and/or cytotoxic therapy and inducing cell apoptosis are provided. Contacting tumor cells to GP88 antagonists (e.g., anti-GP88 antibodies, anti-GP88 antisense nucleic acids, GP88 siRNA, and small molecules) induces apoptosis and restores sensitivity to the antitumorigenic effects of antiestrogen therapy and cytotoxic therapy.

7 Claims, 12 Drawing Sheets

OTHER PUBLICATIONS

Kohler, G. et al., *Continuous cultures of fused cells secreting antibody of predefined specificity*, Nature, vol. 256, 1975, pp. 495-497.

de St. Groth, S.F. et al., *Production of Monoclonal Antibodies: Strategy and Tactics*, Journal of Immunology Methods, 35, 1980, pp. 1-21.

Schreier, M. et al., *Hybridoma Techniques*, Cold Spring Harbor Laboratory, 1980.

Cabilly, S. et al., *Generation of antibody activity from immunoglobulin polypeptide chains produced in Escherichia coli*, Proc. Natl. Acad. Sci. USA, vol. 81, 1984, pp. 3273-3277.

Morrison, S. et al., *Chimeric human antibody molecules: Mouse antigen-binding domains with human constant region domains*, Proc. Natl. Acad. Sci. USA, vol. 81, 1984, pp. 6851-6855.

Liu, A. et al., *Chimeric mouse-human IgG1 antibody that can mediate lysis of cancer cells*, Proc. Natl. Acad. Sci. USA, vol. 84, 1987, pp. 3439-3443.

Better, M. et al., *Escherichia coli Secretion of an Active Chimeric Antibody Fragment*, Science, vol. 240, 1988, pp. 1041-1043.

Riechmann, L. et al., *Reshaping human antibodies for therapy*, Nature, vol. 332, 1988, pp. 323-327.

Baca, M. et al., *Antibody Humanization Using Monovalent Phage Display*, J. Biol. Chem., vol. 272, No. 16, 1997, pp. 10678-10684.

Rosok, M.J. et al., *A Combinatorial Library Strategy for the Rapid Humanization of Anticarcinoma BR96 Fab*, J. Biol. Chem., vol. 271, No. 37, 1996, pp. 22611-22618.

Wahl, R.L. et al., *Improved Radioimaging and Tumor Localization with Monoclonal F(ab')*, The Journal of Nuclear Medicine, vol. 24, No. 4, 1983, pp. 316-325.

Mulshine, J.L., *Clinical Use of a Monoclonal Antibody to Bombesin-lik Peptide in Patients with Lung Cancer*, Annals New York Academy of Sciences, pp. 360-372, 1996.

Munroe, S.H., *Antisense RNA inhibits splicing of pre-mRNA in vitro*, The EMBO Journal, vol. 7, No. 8, 1988, pp. 2523-2532.

Mulis, K.B. et al., *Specific Synthesis of DNA in Vitro via a Polymerase-Catalyzed Chain Reaction*, Methods in Enzymology, vol. 155, 1987, pp. 335-350.

Mercola, D. et al., *Antisense approaches to cancer gene therapy*, Cancer Gene Therapy, vol. 2, No. 1, 1995, pp. 47-59.

Wagner, R. W., *Gene inhibition using antisense oligodeoxynucleotides*, Nature, vol. 372, 1994, pp. 333-335.

Maniatis, T. et al., *Molecular Cloning: A Laboratory Manual*, Cold Spring Harbor Laboratory, 1982.

Brysch, W. et al., *Design and Application of Antisense Oligonucleotides in Cell Culture, in Vivo, and as Therapeutic Agents*, Cellular and Molecular Neurobiology, vol. 14, No. 5, 1994, pp. 557-568.

Helene, C., *Rational Design of Sequence-specific Oncogene Inhibitors Based on Antisense and Antigene Oligonucleotides*, Eur. J. Cancer, vol. 27, No. 11, 1991, pp. 1466-1471.

Giles, R.V. et al., *Optimization of Antisense Oligodeoxynucleotide Structure for Targeting ber-abl\* mRNA*, Blood, vol. 86, No. 2, 1995, pp. 744-754.

Thaler, D.S. et al., *Extending the chemistry that supports genetic information transfer in vivo: Phosphorothioate DNA, phosphorothioate RNA, 2'-O-methyl RNA, and methylphosphonate DNA*, Proc. Natl. Acad. Sci. USA, vol. 93, 1996, pp. 1352-1356.

Gryaznov, S. et al., *Oligonucleotide N3'-P5' phosphoramidates as antisense agents*, Nucleic Acids Research, vol. 24, No. 8, 1996, pp. 1508-1514.

Lappalainen, K. et al., *Cationic liposomes improve stability and intracellular delivery of antisense oligonucleotides into CaSki cells*, Biochimica et Biophysica Acta 1196, 1994, pp. 201-208.

Ensoli, B. et al., *Block of AIDS-Kaposi's Sarcoma (KS) Cell Growth, Angiogenesis, and Lesion Formation in Nude Mice by Antisense Oligonucleotide Targeting Basic Fibroblast Growth Factor*, The Journal of Clinical Investigation, Inc., vol. 94, 1994, pp. 1736-1746.

Peng, B. et al., *Growth Inhibition of Malignant CD5+B (B-1) Cells by Antisense IL-10 Oligonucleotide*, Leukemia Research, vol. 19, No. 3, 1995, pp. 159-167.

Donovan, R.S. et al., *Review: Optimizing inducer and culture conditions for expression of foreign proteins under the control of the lac promoter*, Journal of Industrial Microbiology, 16, 1996, pp. 145-154.

Cenatiempo, Y., *Prokaryotic gene expression in vitro: Transcription-translation coupled systems*, Biochimie, 68, 1986, pp. 505-515.

Gottesman, S., *Bacterial Regulation: Global Regulatory Networks*, Ann, Rev. Genet., 18, 1984, pp. 415-441.

Hamer, D.H. et al., *Regulation In Vivo of a Cloned Mammalian Gene: Cadmium Induces the Transcription of a Mouse Metallothionein Gene in SV40 Vectors*, Journal of Molecular and Applied Genetics, vol. 1, No. 4, 1982, pp. 273-288.

McKnight, S.L., *Functional Relationships between Transcriptional Control Signals of the Thymidine Kinase Gene of Herpes Simplex Virus*, Cell, vol. 31, 1982, pp. 355-365.

Johnston, S.A. et al., *Isolation of the yeast regulatory gene GAL4 and analysis of its dosage effects on the galactose/melibiose regulon*, Proc. Natl. Acad. Sci. USA, 79, 1982, pp. 6971-6975.

Benoist, C. et al., *In vivo sequence requirements of the SV40 early promoter region*, Nature, vol. 290, 1981, pp. 304-310.

Andersson, S. et al., *Cloning, Structure, and Expression of the Mitochondrial Cytochrome P-450 Sterol 26-Hydroxylase, a Bile Acid Biosynthetic Enzyme*, The Journal of Biological Chemistry, vol. 264, No. 14, 1989, pp. 8222-8229.

Sepp-Lorenzino, L. et al., *Insulin and Insulin-like Growth Factor Signaling Are Defective in the MDA MB-468 Human Breast Cancer Cell Line*, Cell Growth & Differentiation, vol. 5, 1994, pp. 1077-1083.

Culouscou, J.M. et al., *Biochemical Analysis of the Epithelin Receptor*, The Journal of Biological Chemistry, vol. 268, No. 14, 1993, pp. 10458-10462.

*Targeted Toxins as Anticancer Agents*, Siegall, C.B., Cancer, vol. 74, No. 3, 1994, pp. 1006-1012.

Zhang et al. *Inhibition of tumorigenicity of the teratoma PC cell line by transfection with antisense cDNA for PC cell-derived growth factor (PCDGF, epithelin/granualin precursor)*, Proc. Natl. Acad. Sci. USA, vol. 95, pp. 14202-14207 (Nov. 1998).

Crooke, S.T. in *Antisense Research and Application* (Stanley T. Crooke, Ed), Springer-Veriag, pp. 1-50, (Jul. 1998).

Branch, A.D. *A good antisense molecule is hard to find* TIBS. vol. 23, pp. 45-50 (Feb. 1998).

Gewirtz, A.M. et al. *Facilitating oligonucleotide delivery: Helping antisense deliver on its promise* Proc. Natl. Acad. Sci. USA. vol. 93, pp. 3161-3163 (Apr. 1996).

Rojanasakul, Y. *Antisense oligonucleotide therapeutics: drug delivery and targeting*, Advanced Drug Delivery Reviews, vol. 18, pp. 115-131 (Jan. 1996).

Anderson, W.F. *Human gene therapy*, Nature, vol. 392, Suppl. pp. 25-30 (Apr. 1998).

Gura, T. *Systems for Identifying New Drugs Are Often Faulty*, Science, vol. 278, pp. 1041-1042 (Nov. 1997).

Resnicoff, M. et al. *Rat Glioblastoma Cells Expressing an Antisense RNA to the Insulin-like Growth Factor-1 (IGF-1) Receptor Are Nontumorigenic and Induce Regression of Wild-Type Tumors*, Cancer Res. vol. 54, pp. 2218-2222 (Apr. 1994).

Zhang Haidi, "Overexpression of PC cell derived growth factor (PCDGF) contributes to the highly tumorigenic properties of producer cell line PC,"DISS. ABSTR. INT., vol. 58, No. 11, 1998, p. 5814-B XP001025915, abstract.

Vijay Bandhari and Andrew Bateman, "Structure and Chromosmal Location of the human granulin gene," Biochemical and Biophysical Research Communications, vol. 188, No. 1, 1992, pp. 57-63, XP001018991, abstract, figure 2.

Bhandari et al., "The Complementary Deoxyribonucleic Acid Sequence, Tissue Distribution, and Cellular Localization of the Rat Granulin Precursor," Endocrinology, vol. 133, No. 6, 1993, pp. 2682-2689.

Sigmund, C.D., "Viewpoint: Are studies in genetically altered mice out of control?" Arteriosclerosis Thrombosis and Vascular Biology, 2000, vol. 20:1425-1429.

Blackshear, P.E. "Genetically engineered rodent models of mammary gland carcinogenesis: An overview," Toxicologic Pathology, 2001, vol. 29:105-116.

Runqing Lu, et al.—"Inhibition of PC cell-derived growth factor (PCDGF, epithelin/granulin precursor) expression by antisense PCDGF cDNA transfection inhibits tumorigenicity of the human breast carcinoma cell line MDA-MB-468," PNAS, vol. 97, No. 8, Apr. 11, 2000, pp. 3993-3998.

Bijay Bhandari et al.—"Isolation and sequence of the granulin precursor cDNA from human bone marrow reveals tandem cystein-rich granulin domains," Proc. Natl. Acad. Sci. USA, vol. 89 Mar. 1992, pp. 1715-1719.

Zhiheng, He et al.—"*Progranulin* Gene Expression Regulates Epithelial Cell Growth and Promotes Tumor Growth in Vivo[1]," Cancer Research 59, Jul. 1, 1999, pp. 3222-3229.

Kumar, R. et al. "Overexpression of HER2 Modulates Bcl-2, Bcl-$X_L$, and Tamoxifen-induced Apoptosis in Human MCF-7 Breast Cancer Cells," Clinical Cancer Research, vol. 2, pp. 1215-1219, Jul. 1996.

Trauth, B.C. et al. "Monoclonal Antibody-Mediated Tumor Regression by Inductilon of Apoptosis," Science, Jul. 1989, pp. 301-305.

Elez, R. et al. "Tumor regression by combination antisense therapy against Plk1 and Bcl-2," Oncogene (2003) vol. 22, pp. 69-80.

Zhang, G-J. et al. "Tamoxifen-induced Apoptosis in Breast Cancer Cells Relates to Down-Regulation of bcl-2, but not bax and bcl-$X_L$, without Alteration of p53 Protein Levels," Clinical Cancer Research, vol. 5, Oct. 1999, pp. 2971-2977.

* cited by examiner

Mouse GP88 cDNA

```
C GGA CCC CGA CGC AGA CAG ACC ATG TGG GTC CTG ATG AGC TGG CTG    46
                                M   W   V   L   M   S   W   L    8

GCC TTC GCG GCA GGG CTG GTA GCC GGA ACA CAG TGT CCA GAT GGG CAG   94
 A   F   A   A   G   L   V   A   G   T   Q   C   P   D   G   Q   24

TTC TGC CCT GTT GCC TGC TGC CTT GAC CAG GGA GGA GCC AAC TAC AGC  142
 F   C   P   V   A   C   C   L   D   Q   G   G   A   N   Y   S   40

TGC TGT AAC CCT CTT CTG GAC ACA TGG CCT AGA ATA ACG AGC CAT CAT  190
 C   C   N   P   L   L   D   T   W   P   R   I   T   S   H   H   56

CTA GAT GGC TCC TGC CAG ACC CAT GGC CAC TGT CCT GCT GGC TAT TCT  238
 L   D   G   S   C   Q   T   H   G   H   C   P   A   G   Y   S   72

TGT CTT CTC ACT GTG TCT GGG ACT TCC AGC TGC TGC CCG TTC TCT AAG  286
 C   L   L   T   V   S   G   T   S   S   C   C   P   F   S   K   88

GGT GTG TCT TGT GGT GAT GGC TAC CAC TGC TGC CCC CAG GGC TTC CAC  334
 G   V   S   C   G   D   G   Y   H   C   C   P   Q   G   F   H  104

TGT AGT GCA GAT GGG AAA TCC TGC TTC CAG ATG TCA GAT AAC CCC TTG  382
 C   S   A   D   G   K   S   C   F   Q   M   S   D   N   P   L  120

GGT GCT GTC CAG TGT CCT GGG AGC CAG TTT GAA TGT CCT GAC TCT GCC  430
 G   A   V   Q   C   P   G   S   Q   F   E   C   P   D   S   A  136

ACC TGC TGC ATT ATG GTT GAT GGT TCG TGG GGA TGT TGT CCC ATG CCC  478
 T   C   C   I   M   V   D   G   S   W   G   C   C   P   M   P  152

CAG GCC TCT TGC TGT GAA GAC AGA GTG CAT TGC TGT CCC CAT GGG GCC  526
 Q   A   S   C   C   E   D   R   V   H   C   C   P   H   G   A  168

TCC TGT GAC CTG GTT CAC ACA CGA TGC GTT TCA CCC ACG GGC ACC CAC  574
 S   C   D   L   V   H   T   R   C   V   S   P   T   G   T   H  184

ACC CTA CTA AAG AAG TTC CCT GCA CAA AAG ACC AAC AGG GCA GTG TCT  622
 T   L   L   K   K   F   P   A   Q   K   T   N   R   A   V   S  200

TTG CCT TTT TCT GTC GTG TGC CCT GAT GCT AAG ACC CAG TGT CCC GAT  670
 L   P   F   S   V   V   C   P   D   A   K   T   Q   C   P   D  216
```

FIG. 1A

Mouse GP88 cDNA (continued)

```
GAT TCT ACC TGC TGT GAG CTA CCC ACT GGG AAG TAT GGC TGC TGT CCA    718
 D   S   T   C   C   E   L   P   T   G   K   Y   G   C   C   P    232

ATG CCC AAT GCC ATC TGC TGT TCC GAC CAC CTG CAC TGC TGC CCC CAG    766
 M   P   N   A   I   C   C   S   D   H   L   H   C   C   P   Q    248

GAC ACT GTA TGT GAC CTG ATC CAG AGT AAG TGC CTA TCC AAG AAC TAC    814
 D   T   V   C   D   L   I   Q   S   K   C   L   S   K   N   Y    264

ACC ACG GAT CTC CTG ACC AAG CTG CCT GGA TAC CCA GTG AAG GAG GTG    862
 T   T   D   L   L   T   K   L   P   G   Y   P   V   K   E   V    280

AAG TGC GAC ATG GAG GTG AGC TGC CCT GAA GGA TAT ACC TGC TGC CGC    910
 K   C   D   M   E   V   S   C   P   E   G   Y   T   C   C   R    296

CTC AAC ACT GGG GCC TGG GGC TGC TGT CCA TTT GCC AAG GCC GTG TGT    958
 L   N   T   G   A   W   G   C   C   P   F   A   K   A   V   C    312

TGT GAG GAT CAC ATT CAT TGC TGC CCG GCA GGG TTT CAG TGT CAC ACA    1006
 C   E   D   H   I   H   C   C   P   A   G   F   Q   C   H   T    328

GAG AAA GGA ACC TGC GAA ATG GGT ATC CTC CAA GTA CCC TGG ATG AAG    1054
 E   K   G   T   C   E   X   G   I   L   Q   V   P   W   M   K    344

AAG GTC ATA GCC CCC CTC CGC CTG CCA GAC CCA CAG ATC TTG AAG AGT    1102
 K   V   I   A   P   L   R   L   P   D   P   Q   I   L   K   S    360

GAT ACA CCT TGT GAT GAC TTC ACT AGG TGT CCT ACA AAC AAT ACC TGC    1150
 D   T   P   C   D   D   F   T   R   C   P   T   N   N   T   C    376

TGC AAA CTC AAT TCT GGG GAC TGG GGC TGC TGT CCC ATC CCA GAG GCT    1198
 C   K   L   N   S   G   D   W   G   C   C   P   I   P   E   A    392

GTC TGC TGC TCA GAC AAC CAG CAT TGC TGC CCT CAG GGC TTC ACA TGT    1246
 V   C   C   S   D   N   Q   H   C   C   P   Q   G   F   T   C    408

CTG GCT CAG GGG TAC TGT CAG AAG GGA GAC ACA ATG GTG GCT GGC CTG    1294
 L   A   Q   G   Y   C   Q   K   G   D   T   M   V   A   G   L    424

GAG AAG ATA CCT GCC CGC CAG ACA ACC CCG CTC CAA ATT GGA GAT ATC    1342
 E   K   I   P   A   R   Q   T   T   P   L   Q   I   G   D   I    440
```

FIG. 1B

Mouse GP88 cDNA (continued)

```
GGT TGT GAC CAG CAT ACC AGC TGC CCA GTA GGG CAA ACC TGC TGC CCA    1390
 G   C   D   Q   H   T   S   C   P   V   G   Q   T   C   C   P     456

AGC CTC AAG GGA AGT TGG GCC TGC TGC CAG CTG CCC CAT GCT GTG TGC    1438
 S   L   K   G   S   W   A   C   C   Q   L   P   H   A   V   C     472

TGT GAG GAC CGG CAG CAC TGT TGC CCG GCC GGG TAC ACC TGC AAC GTG    1486
 C   E   D   R   Q   H   C   C   P   A   G   Y   T   C   N   V     488

AAG GCG AGG ACC TGT GAG AAG GAT GTC GAT TTT ATC CAG CCT CCC GTG    1534
 K   A   R   T   C   E   K   D   V   D   F   I   Q   P   P   V     504

CTC CTG ACC CTC GGC CCT AAG GTT GGG AAT GTG GAG TGT GGA GAA GGG    1582
 L   L   T   L   G   P   K   V   G   N   V   E   C   G   E   G     520

CAT TTC TGC CAT GAT AAC CAG ACC TGT TGT AAA GAC AGT GCA GGA GTC    1630
 H   F   C   H   D   N   Q   T   C   C   K   D   S   A   G   V     536

TGG GCC TGC TGT CCC TAC CTA AAG GGT GTC TGC TGT AGA GAT GGA CGT    1678
 W   A   C   C   P   Y   L   K   G   V   C   C   R   D   G   R     552

CAC TGT TGC CCC GGT GGC TTC CAC TGT TCA GCC AGG GGA ACC AAG TGT    1726
 H   C   C   P   G   G   F   H   C   S   A   R   G   T   K   C     568

TTG CGA AAG AAG ATT CCT CGC TGG GAC ATG TTT TTG AGG GAT CCG GTC    1774
 L   R   K   K   I   P   R   W   D   M   F   L   R   D   P   V     584

CCA ACA CCG CTA CTG TAA GGA AGG GCT ACA GAC TTA AGG AAC TCC ACA    1822
 P   R   P   L   L   *                                              589

GTC CTG GGA ACC TGT TCG AGG GTA CCA CTA CTC AGG CCT CCC TAG        1870
CGC CTC CTC CCC TAA CGT CTC CCC GGC CTA CTC ATC CTG AGT CAC CCT   1918
ATC ACC ATG GGA GGT GGA GCC TCA AAC TAA AAC CTT CTT TTA TGG AAA   1966
GAA GGC TGT GGC CAA AAG CCC CGT ATC AAA CTG CCA TTT CTT CCG GTT   2014
TCT GTG GAC CTT GTG GCC AGG TGC TCT TCC CGA GCC ACA GGT GTT CTG   2062
TGA GCT TGC TTG TGT GTG TGT GCG CGT GTG CGT GTG TTG CTC AAA TAA   2110
AGT TTG TAC GCT TTC TGA AAA AAA AAA                                2137
```

FIG. 1C

Nucléotide sequence of human granulin/epithelin precursor (human GP88).
Human Granulin Genbank M75161$ cgcaggcaga ccatgtggac cttggtgagc tgggtggcct taacagcagg gctggtggct
ggaacgcggt gcccagatgg tcagttctgc cctgtggcct gctgcctgga ccccggagga
gccagctaca gctgctgccg tccccttctg gacaaatggc ccacaacact gagcaggcat
ctgggtggcc cctgccaggt tgatgcccac tgctctgccg gccactcctg catctttacc
gtctcaggga cttccagttg ctgcccttc ccagaggccg tggcatgcgg ggatggccat
cactgctgcc cacggggctt ccactgcagt gcagacggga gatcctgctt ccaaagatca
ggtaacaact ccgtgggtgc catccagtgc cctgatagtc agttcgaatg cccggacttc
tccacgtgct gtgttatggt cgatggctcc tgggggtgct gccccatgcc ccaggcttcc
tgctgtgaag acagggtgca ctgctgtccg cacggtgcct tctgcgacct ggttcacacc
cgctgcatca cacccacggg caccacccc ctggcaaaga agctccctgc cagaggact
aacagggcag tggccttgtc cagctcggtc atgtgtccgg acgcacggtc ccggtgccct
gatggttcta cctgctgtga gctgcccagt gggaagtatg gctgctgccc aatgcccaac
gccacctgct gctccgatca cctgcactgc tgcccccaag acactgtgtg tgacctgatc
cagagtaagt gcctctccaa ggagaacgct accacggacc tcctcactaa gctgcctgcg
cacacagtgg gcgatgtgaa atgtgacatg gaggtgagct gcccagatgg ctataccctgc
tgccgtctac agtcgggggc ctggggctgc tgcccttta cccaggctgt gtgctgtgag
gaccacatac actgctgtcc cgcggggttt acgtgtgaca cgcagaaggg tacctgtgaa
cagggcccc accaggtgcc ctggatggag aaggccccag ctcacctcag cctgccagac
ccacaagcct tgaagagaga tgtccctgt gataatgtca gcagctgtcc ctcctccgat
acctgctgcc aactcacgtc tggggagtgg ggctgctgtc aatcccaga ggctgtctgc
tgctcggacc accagcactg ctgcccccag cgatacacgt gtgtagctga ggggcagtgt
cagcgaggaa gcgagatcgt ggctggactg gagaagatgc ctgcccgccg cggttcctta
tcccacccca gagacatcgg ctgtgaccag cacaccagct gcccggtggg cggaacctgc
tgcccgagcc agggtgggag ctgggcctgc tgccagttgc cccatgctgt gtgctgcgag
gatcgccagc actgctgccc ggctggctac acctgcaacg tgaaggctcg atcctgcgag
aaggaagtgg tctctgccca gcctgccacc ttcctggccc gtagccctca cgtgggtgtg
aaggacgtgg agtgtgggga aggacacttc tgccatgata accagacctg ctgccgagac
aaccgacagg gctgggcctg ctgtcccta gcccagggcg tctgttgtgc tgatcggcgc
cactgctgtc ctgctggctt ccgctgcgca cgcagggta ccaagtgttt gcgcagggag
gccccgcgct gggacgcccc tttgagggac ccagccttga cagctgct gtgagggaca
gtactgaaga ctctgcagcc ctcgggaccc cactcggagg gtgccctctg ctcaggcctc
gtactgaaga ctctgcagcc ctcgggaccc cactcggagg gtgccctctg ctcaggcctc
cctagcacct cccctaacc aaattctccc tggaccccat tctgagctcc ccatcaccat
gggaggtggg gcctcaatct aaggcccttc cctgtcagaa gggggttgag gcaaaagccc
attacaagct gccatcccct ccccgtttca gtggacctg tggccaggtg cttttcccta
tccacagggg tgtttgtgtg ttgggtgtgc tttcaataaa gtttgtcact ttctt*

FIG. 2A

Amino-acid sequence of human granulin/epithelin precursor (human GP88).

MWTLVSWVALTAGLVAGTRCPDGQFCPVACCLDPGGASYSCCRP
LLDKWPTTLSRHLGGPCQVDAHCSAGHSCIFTVSGTSSCCPFPEAVACGDGHHCCPRG
FHCSADGRSCFQRSGNNSVGAIQCPDSQFECPDFSTCCVMVDGSWGCCPMPQASCCED
RVHCCPHGAFCDLVHTRCITPTGTHPLAKKLPAQRTNRAVALSSSVMCPDARSRCPDG
STCCELPSGKYGCCPMPNATCCSDHLHCCPQDTVCDLIQSKCLSKENATTDLLTYLPA
HTVGDVKCDMEVSCPDGYTCCRLQSGAWGCCPFTQAVCCEDHIHCCPAGFTCDTQKGT
CEQGPHQVPWMEKAPAHLSLPDPQALKRDVPCDNVSSCPSSDTCCQLTSGEWGCCPIP
EAVCCSDHQHCCPQRYTCVAEGQCQRGSEIVAGLEKMPARRGSLSHPRDIGCDQHTSC
PVGGTCCPSQGGSWACCQLPHAVCCEDRQHCCPAGYTCNVKARSCEKEVVSAQPATFL
ARSPHVGVKDVECGEGHFCHDNQTCCRDNRQGWACCPYAQGVCCADRRHCCPAGFRCA
RRGTKCLRREAPRWDAPLRDPALRQLL*

FIG. 2B

Mouse GP88 protein sequence

MWVLMSWLAFAAGLVAG 17

TQCPDGQF-CPVA--CCLDQG-GANYSCCNPLLDTWPRITSHHL 57
    :   :::       :       ::::
DGSC-QTHGHCPAGY-SCLLTVSGTS-SCCPFSKGVSCGDGYHCCPQGFHCSADGKSCFQMSDNPL 120
   :     :::         :       :::: ::::        ::::
GAVQCPGSQFECPDSATCCIMVD-G-SWGCCPMPQASCCEDRVHCCPHGASCDLVHTRCVSPTGTHTLLKKFPAQKTNAAVSLPFS 204    g
          ::: :::         :       ::::         ::::
VVCPDAKTQCPDDSTCCELP-TGK-YGCCPMPNAICCSDHLHCCPQDTVCDLIQSKCLSKNYTDLLTKLPGYPVK 278    f
   :     :::         :       ::::         ::::       •
EVKC-DMEVSCPEGYTCCALN-TGA-WGCCPFAKAVCCEEDHIHCCPAGFOCHTEKGICEMGILQVPWMKKVIAPRRLPDPQILKS 360    2,B
   :     :::         :       ::::         ::::
DIPCDDFTR-CPTNNTCCKLN-SGD-WGCCPIPEAVCCSDNQHCCPQGFTCLAQGY-CQKGDTMVAGLEKIPARQTTPLQIG 438    1,A
   :     :::         :       ::::         ::::
DIGCDuHT-SCPVGQTCCPSLK-G-SWACCQLPHAVCCEDRQHCCPAGYTCNVKARTCEKDVDFIQPPVLLTLGPKVG 513    C
   :     :::         :       ::::         ::::
NVECGEGHF-CHDNQTCCKDSA-GV-WACCPYLKGVCCRDGRHCCPGGFHCSARGTKCLAKKIPRWDMFLADPVPRPLL 589    D
                                                                                        e consensus sequence:

C......C.....CC......G......CC.........CC.D..HCCP....C........C 1,2:mouse epithelin 1,2.
A,B,C,D,e,f,g: granulin A,B,C,D,E,F,G;N-terminus of granulin A,B,C,D have been sequenced.
Mouse epithelin precursor sequence is from Plowman et al.(1992).

FIG. 3

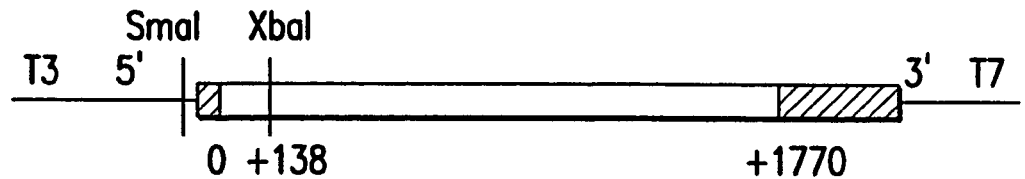
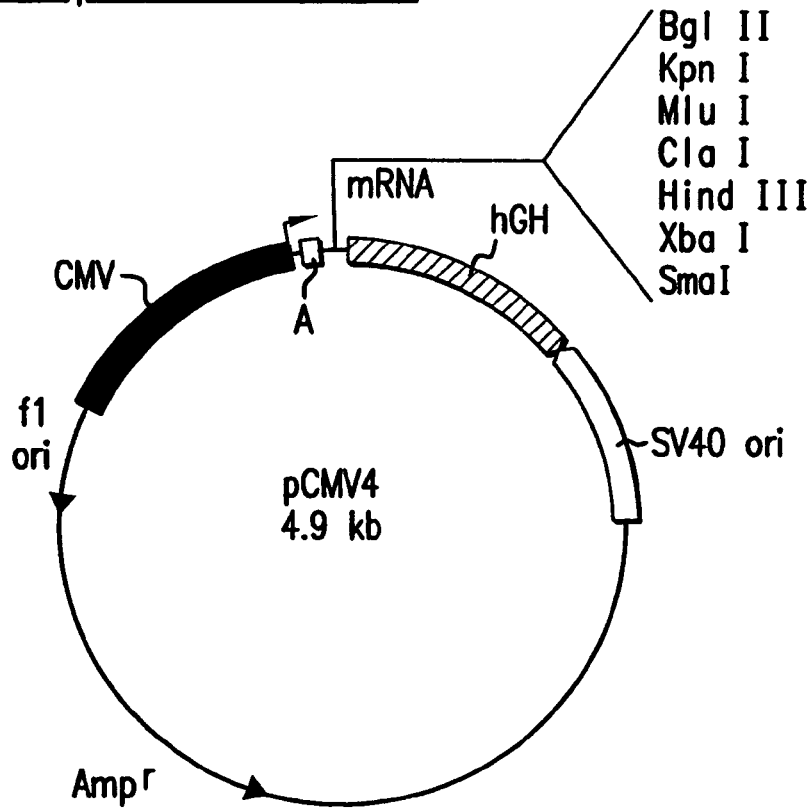
FIG. 4

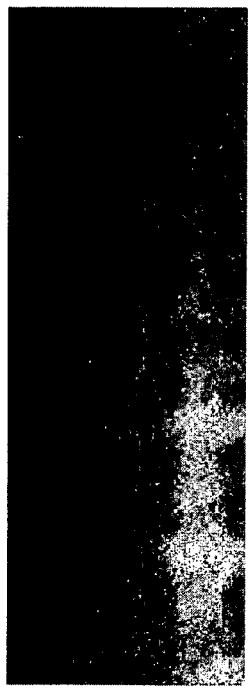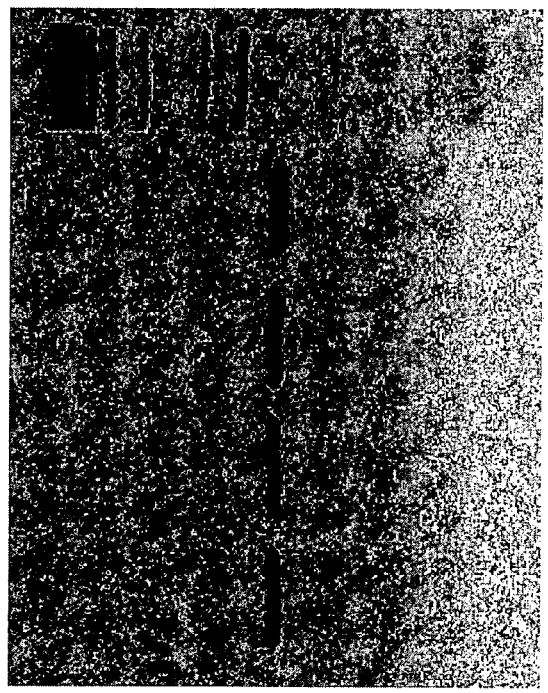
Tamoxifen resistant MCF-7 cells
FIG. 6

O4 cells (GP88 overexpressing tamoxifen resistant MCF-7 cells)

COMPOSITIONS AND METHODS FOR RESTORING SENSITIVITY OF TUMOR CELLS TO ANTITUMOR THERAPY AND INDUCING APOPTOSIS

CROSS-REFERENCE TO RELATED APPLICATIONS

This application claims the benefit of U.S. Provisional Application No. 60/480,439, filed Jun. 23, 2003. The following U.S. Patents and U.S. Patent Publications are expressly incorporated by reference herein in their entirety: U.S. Pat. No. 6,720,159; U.S. Pat. No. 6,309,826; U.S. patent Publication No. 2003/0099646; U.S. patent Publication No. 2003/0215445; and U.S. patent Publication No. 2002/0025543.

FIELD OF THE INVENTION

This invention relates to cell biology, physiology and medicine, and concerns an 88 kDa glycoprotein growth factor ("GP88") and compositions and methods which affect the expression and biological activity of GP88. This invention also relates to kit products, compositions and methods which are useful for diagnosis and treatment of diseases including cancer.

BACKGROUND OF THE INVENTION

The proliferation and differentiation of cells in multicellular organisms is subject to a highly regulated process. A distinguishing feature of cancer cells is the absence of control over this process; proliferation and differentiation become deregulated resulting in uncontrolled growth. Significant research efforts have been directed toward better understanding this difference between normal and tumor cells. One area of research focus is growth factors and, more specifically, autocrine growth stimulation.

Growth factors are polypeptides which carry messages to cells concerning growth, differentiation, migration and gene expression. Typically, growth factors are produced in one cell and act on another cell to stimulate proliferation. However, certain malignant cells, in culture, demonstrate a greater or absolute reliance on an autocrine growth mechanism. Malignant cells which observe this autocrine behavior circumvent the regulation of growth factor production by other cells and are therefore unregulated in their growth.

Study of autocrine growth control advances understanding of cell growth mechanisms and can lead to important advances in the diagnosis and treatment of cancer. Toward this end, a number of growth factors have been studied, including insulin-like growth factors ("IGF1" and "IGF2"), gastrin-releasing peptide ("GRP"), transforming growth factors alpha and beta ("TGF-a" and "TGF-b"), and epidermal growth factor ("EGF").

The present invention is directed to a recently discovered growth factor. This growth factor was first discovered in the culture medium of highly tumorigenic "PC cells," an insulin-independent variant isolated from the teratoma derived adipogenic cell line 1246. This growth factor is referred to herein as "GP88" or "GP88." GP88 has been purified and structurally characterized. Amino acid sequencing of GP88 indicates that GP88 has amino acid sequence similarities with the mouse granulin/epithelin precursor.

Granulins/epithelins ("grn/epi") are 6kDa polypeptides and belong to a novel family of double cysteine rich polypeptides. U.S. Pat. No. 5,416,192 (Shoyab et al.) is directed to 6 kDa epithelins, particularly epithelin 1 and epithelin 2. According to Shoyab, both epithelins are encoded by a common 63.5 kDa precursor, which is processed into smaller forms as soon as it is synthesized, so that the only natural products found in biological samples are the 6 kDa forms. Shoyab et al. teaches that the epithelin precursor is biologically inactive.

Contrary to the teachings of Shoyab et al., the inventor's laboratory has demonstrated that the precursor is not always processed as soon as it is synthesized. Studies, conducted in part by this inventor, have demonstrated that the precursor (i.e., GP88) is in fact secreted as an 88kDa glycoprotein with an N-linked carbohydrate moiety of 20 kDa. Analysis of the N-terminal sequence of GP88 indicates that GP88 starts at amino acid 17 of the grn/epi precursor, demonstrating that the first 17 amino acids from the protein sequence deduced from the precursor cDNA correspond to a signal peptide compatible with targeting for membrane localization or for secretion. Also in contrast to the teachings of Shoyab et al., GP88 is biologically active and has growth promoting activity, particularly as an autocrine growth factor for the producer cells.

Multi-cellular organisms require a careful balance between the production and destruction of cells in tissues throughout the body. Apoptosis, or programmed cell death, is a controlled process by which damaged cells or cells replicating outside of normal cellular control can be eliminated without causing the tissue destruction and inflammatory responses often associated with acute injury and necrosis.

Recent studies indicate that apoptosis is controlled through a metabolic pathway which may be induced by a variety of signals (e.g., hormones, serum growth factor deprivation, chemotherapeutic agents, ionizing radiation, and viral infection). See, e.g., U.S. Pat. Nos. 6,586,395 and 6,570,002. The Bcl-2 family of genes regulate apoptosis in many cell types. The normal function of Bcl-2 is to block apoptosis in response to a variety of signals (e.g., radiation, hyperthermia, growth factor withdrawal, glucocorticoids, and multiple classes of chemotherapeutic agents). Id. Thus, blocking the activity of Bcl-2 induces apoptosis. Zhang et al., Clinical Cancer Research, 5:2971-2977 (October 1999). For example, the anti-estrogen compound tamoxifen down regulates Bcl-2 and thus induces apoptosis in breast cancer cells. Id. In addition to inhibiting the growth promoting effect of estrogen, tamoxifen has also been shown to induce programmed cell death in breast cancer cell lines and in clinical samples. Failure to undergo apoptosis in response to tamoxifen confers tamoxifen resistance.

Anti-estrogen therapy is widely used for the treatment of breast cancer. Tamoxifen has been the major agent used for this purpose. The activity of tamoxifen is typically observed in breast tumors that are estrogen receptor positive, since estrogen is the major growth stimulator for these types of tumors. However, after prolonged anti-hormonal therapy, breast cancer can progress from an estrogen sensitive to insensitive state. Breast tumors that were previously growth inhibited by tamoxifen and other anti-estrogen compounds then become resistant to anti-estrogen treatment.

The morphological changes induced by tamoxifen are characteristic of the changes induced by apoptosis. Up-regulation of Bcl-2 by HER2 suppresses tamoxifen-induced apoptosis in breast cancer cells. Kumar et al., Clin. Cancer Res. 1996 Jul.2(7):1215-9. Thus, modulation of Bcl-2 levels provides a mechanism for inducing apoptosis. Inducing apoptosis leads to tumor regression by eliminating, shrinking, and destroying tumor cells. Trauth et al., Science. 1989

Jul. 21;245(4915):301-5. Administration of antisense oligonucleotides directed to the anti-apoptotic Bcl-2 gene induces tumor regression in mice in vivo. Elez et al., Oncogene (2003) 22: 69-80.

What is needed are new methods and compositions for inducing apoptosis and restoring sensitivity to the antitumorigenic effects of antiestrogen therapy and cytotoxic therapy.

BRIEF SUMMARY OF THE INVENTION

The inventor has unexpectedly discovered that a glycoprotein (GP88), which is expressed in a tightly regulated fashion in normal cells, is overexpressed and unregulated in highly tumorigenic cells derived from the normal cells, that GP88 acts as a stringently required growth stimulator for the tumorigenic cells and that inhibition of GP88 expression or action in the tumorigenic cells results in an inhibition of the tumorigenic properties of the overproducing cells.

In one embodiment of the invention, sensitivity to the antitumorigenic effects of antiestrogens and/or cytotoxic compounds is restored by administering a GP88 antagonist to a tumor cell. In another embodiment, the GP88 antagonist can be administered together with or sequentially with an antiestrogen or cytotoxic (e.g., chemotherapeutic) compound. Tumor cells overexpressing GP88 are growth stimulated and are resistant to treatment by tamoxifen and other anti-estrogens. Administration of a GP88 antagonist to a tumor cell restores sensitivity to (1) tamoxifen and other antiestrogens (e.g., raloxifene, aromatase inhibitors) and/or (2) cytoxic or chemotherapeutic agents (e.g., Altretamine, Bleomycin, Busulphan, Calcium Folinate, Capecitabine, Carboplatin, Carmustine, Chlorambucil, Cisplatin, Cladribine, Crisantaspase, Cyclophosphamide, Cytarabine, Dacarbazine, Dactinomycin, Daunorubicin, Docetaxel, Doxorubicin, Epirubicin, Etoposide, Fludarabine, Fluorouracil, Gemcitabine, Hydroxyurea, Idarubicin, Ifosfamide, Irinotecan, Liposomal doxorubicin, Lomustine, Melphalan, Mercaptopurine, Methotrexate, Mitomycin, Mitoxantrone, Oxaliplatin, Paclitaxel, Pentostatin, Procarbazine, Raltitrexed, Streptozocin, Tegafur-uracil, Temozolomide, Thiotepa, Tioguanine/Thioguanine, Topotecan, Treosulfan, Vinblastine, Vincristine, Vindesine, and Vinorelbine) and combinations thereof. GP88 antagonists can also be administered either before or after administration of an antiestrogen and/or a cytotoxic compound to restore sensitivity to the antiestrogen and/or cytotoxic compound.

The invention also provides methods and compositions for inducing apoptosis by administering a GP88 antagonist to a tumor cell. Induction of apoptosis can be determined, for example, by measuring the level of Bcl-2 protein or mRNA, measuring the ability of the cell to cleave PARP (poly (ADP ribose) polymerase), or evaluating the appearance or volume of the tumor cell or cells.

This invention also provides GP88 antagonizing compositions capable of inhibiting the expression or activity of GP88, methods for treating diseases associated with a defect in GP88 quantity or activity such as cancer, including, but not limited to, cancer in mammalian blood, cerebrospinal fluid, serum, plasma, prostate, bladder, nasopharynx, head and neck, cervix, neural tissue, thyroid, pancreas, urine, nipple aspirate, liver, kidney, breast, bone, bone marrow, testes, brain, neural, ovary, skin, and lung, methods for determining the susceptibility of a subject to diseases associated with a defect in GP88 expression or action, methods for measuring susceptibility to GP88 antagonizing therapy, and methods, reagents, and kits for the in vitro and in vivo detection of GP88 and tumorigenic activity in cells.

Additional objects and advantages of the invention will be set forth in part in the description that follows, and in part will be obvious from the description, or may be learned by the practice of the invention.

The present invention also provides compositions and methods for diagnosis and treatment of diseases, such as breast cancer, in which cells exhibit an altered expression of GP88 or altered response to GP88. Use of the term "altered expression" herein means increased expression or overexpression of GP88 by a factor of at least two-fold, and at times by a factor of 10 or more, based on the level of mRNA or protein as compared to corresponding normal cells or surrounding peripheral cells. The term "altered expression" also means expression which became unregulated or constitutive without being necessarily elevated. Use of the terms increased or altered "response" to GP88 means a condition wherein increase in any of the biological functions (e.g., growth, differentiation, viral infectivity) conferred by GP88 results in the same or equivalent condition as altered expression of GP88.

Use of the term "GP88" or "PCDGF" herein means epithelin/granulin precursor (also known as progranulin), in cell extracts and extracellular fluids, and is intended to include not only GP88 according to the amino acid sequences included in FIGS. 1-3, which are of mouse and human origins, but also GP88 of other species. In addition, the term also includes functional derivatives thereof having additional components such as a carbohydrate moiety including a glycoprotein or other modified structures.

Also intended by the term GP88 or PCDGF is any polypeptide fragment having at least 10 amino-acids present in the above mentioned sequences. Sequences of this length are useful as antigens and for making immunogenic conjugates with carriers for the production of antibodies specific for various epitopes of the entire protein. Such polypeptides are useful in screening such antibodies and in the methods directed to detection of GP88 in biological fluids. It is well known in the art that peptides are useful in generation of antibodies to larger proteins. In one embodiment of this invention, it is shown that peptides from 12-19 amino-acids in length have been successfully used to develop antibodies that recognize the full length GP88.

The polypeptide of this invention may exist covalently or non-covalently bound to another molecule. For example, it may be fused to one or more other polypeptides via one or more peptide bonds such as glutathione transferase, polyhistidine, or myc tag.

The polypeptide is sufficiently large to comprise an antigenetically distinct determinant or epitope which can be used as an immunogen to reproduce or test antibodies against GP88 or a functional derivative thereof.

One embodiment includes the polypeptide substantially free of other mammalian peptides. GP88 of the present invention can be biochemically or immunochemically purified from cells, tissues or a biological fluid. Alternatively, the polypeptide can be produced by recombinant means in a prokaryotic or eukaryotic expression system and host cells.

"Substantially free of other mammalian polypeptides" reflects the fact that the polypeptide can be synthesized in a prokaryotic or a non-mammalian or mammalian eukaryotic organism, if desired. Alternatively, methods are well known for the synthesis of polypeptides of desired sequences by chemical synthesis on solid phase supports and their subsequent separation from the support. Alternatively, the protein can be purified from tissues or fluids of mammals where it naturally occurs so that it is at least 90% pure (on a weight basis) or even 99% pure, if desired, of other mammalian polypeptides, and is therefore substantially free from them. This can be achieved by subjecting the tissue extracts or fluids to standard protein purification such as on immuno-absorbants bearing antibodies reactive against the protein. One embodiment of the present invention describes purification methods for the purification of naturally occurring GP88 and of recombinant GP88 expressed in baculovirus infected insect cells, and in mammalian cells. Alternatively, purification from such tissues or fluids can be achieved by a combination of methods known in the art.

As an alternative to a native purified or recombinant glycoprotein or polypeptide, "GP88" is intended to also include functional derivatives. By functional derivative is meant a "fragment," "variant," "analog," or "chemical derivative" of the protein or glycoprotein as defined below. A functional derivative retains at least a portion of the function of the full length GP88 which permits its utility in accordance with the present invention.

A "fragment" of GP88 refers to any subset of the molecule that is a shorter peptide retaining the tumorigenic properties of GP88. This corresponds for example but is not limited to regions such as K19T and S14R for mouse GP88, and E19V and A14R (equivalent to murine K19T and S14R, respectively) for human GP88.

A "variant" of GP88 refers to a molecule substantially similar to either the entire peptide or a fragment thereof. Variant peptides may be prepared by direct chemical synthesis of the variant peptide using methods known in the art.

Alternatively, amino acid sequence variants of the peptide can be prepared by modifying the DNA which encodes the synthesized protein or peptide. Such variants include, for example, deletions, insertions, or substitutions of residues within the amino-acid sequence of GP88. Any combination of deletion, insertion, and substitution may also be made to arrive at the final construct, provided the final construct possesses the desired activity. The mutation that will be made in the DNA encoding the variant peptide must not alter the reading frame and preferably will not create complementary regions that could produce secondary mRNA structures. At the genetic level, these variants are prepared by site directed mutagenesis (8) of nucleotides in the DNA encoding the peptide molecule thereby producing DNA encoding the variant, and thereafter expressing the DNA in recombinant cell culture. The variant typically exhibits the same qualitative biological activity as the nonvariant peptide.

An "analog" of GP88 protein refers to a non-natural molecule substantially similar to either the entire molecule or a fragment thereof.

A "chemical derivative" contains additional chemical moieties not normally a part of the peptide or protein. Covalent modifications of the peptide are also included within the scope of this invention. Such modifications may be introduced into the molecule by reacting targeted amino-acid residues of the peptide with an organic derivatizing agent that is capable of reacting with selected side chains or terminal amino-acid residues. Most commonly derivatized residues are cysteinyl, histidyl, lysinyl, arginyl, tyrosyl, glutaminyl, asparaginyl and amino terminal residues. Hydroxylation of proline and lysine, phosphorylation of hydroxyl groups of seryl and threonyl residues, methylation of the alpha-amino groups of lysine, histidine, and histidine side chains, acetylation of the N-terminal amine and amidation of the C-terminal carboxylic groups. Such derivatized moieties may improve the solubility, absorption, biological half life and the like. The moieties may also eliminate or attenuate any undesirable side effect of the protein and the like. In addition, derivatization with bifunctional agents is useful for cross-linking the peptide to water insoluble support matrices or to other macromolecular carriers. Commonly used cross-linking agents include glutaraldehyde, N-hydroxysuccinimide esters, homobifunctional imidoesters, 1,1-bis(-diazoloacetyl)-2-phenylethane, and bifunctional maleimides. Derivatizing agents such as methyl-3-[9p-azidophenyl)]dithiopropioimidate yield photoactivatable intermediates that are capable of forming crosslinks in the presence of light. Alternatively, reactive water-insoluble matrices such as cyanogen bromide activated carbohydrates and the reactive substrates described in U.S. Pat. Nos. 3,969,287 and 3,691,016 may be employed for protein immobilization.

Use of the term GP88 antagonist or GP88 "antagonizing agents" herein means any composition that inhibits or blocks GP88 expression, production or secretion, or any composition that inhibits or blocks the biological activity of GP88. This can be achieved by any mode of action such as but not limited to the following:

(A) GP88 antagonizing agents include any reagent or molecule inhibiting GP88 expression or production including but not limited to: (1) antisense GP88 DNA or RNA molecules that inhibit GP88 expression by inhibiting GP88 translation; (2) small inhibitory or "siRNA" that inhibit GP88 expression (3) reagents (hormones, growth factors, small molecules) that inhibit GP88 mRNA and/or protein expression at the transcriptional, translational or post-translational levels; (4) factors, reagents or hormones that inhibit GP88 secretion.

(B) GP88 antagonizing agents also include any reagent or molecule that will inhibit GP88 action or biological activity such as but not limited to: (1) neutralizing antibodies to GP88 that bind the protein and prevent it from exerting its biological activity; (2) antibodies to the GP88 receptor that prevent GP88 from binding to its receptor and from exerting its biological activity; (3) competitive inhibitors of GP88 binding to its receptors; (4)) small molecule antagonists; and (5) inhibitors of GP88 signaling pathways.

In one embodiment of the invention, the GP88 antagonizing agents are antisense oligonucleotides to GP88. The antisense oligonucleotides preferably inhibit GP88 expression by inhibiting translation of the GP88 protein. Antisense oligonucleotides may be formed from DNA or RNA. In another embodiment, the GP88 antagonizing agents are small-inhibitory RNA molecules (siRNA or RNAi). siRNA are double-stranded RNA molecules capable of suppressing the expression of a target gene.

GP88 antagonizing agents may comprise small molecules (e.g., reagents, factors or hormones) that inhibit GP88 expression. For example, embodiments of the invention provide small molecules that (1) inhibit GP88 post-translational modification and its secretion, (2) block GP88 activity by competing with GP88 for binding to GP88 cell surface receptors, (3) inhibit the GP88 signal transduction pathway (e.g., biochemical interactions induced by GP88 binding to its receptor on the cell surface), or (4) interfere or inhibit with the GP88 receptor. Small molecules may be synthesized in order to bind to or associate with particular active sites on GP88, GP88 cell surface receptors, or other molecules. Small molecules can also be derived from natural sources and modified to bind to and/or inhibit GP88, GP88 cell surface receptors, or other molecules.

The antibodies of the invention (neutralizing and others) are preferably used as a treatment for breast cancer, other cancers, or other diseases in cells which exhibit an increased expression of GP88 (e.g., neuroblastoma, glioblastoma, astrocytoma, sarcomas, and cancers of the prostate, blood, cerebrospinal fluid, liver, kidney, breast, head and neck, pharynx, thyroid, pancreas, stomach, colon, colorectal, uterus, cervix, bone, bone marrow, testes, brain, neural tissue, ovary, skin, and lung). By the term "neutralizing" it shall be understood that the antibody has the ability to inhibit or block the normal biological activity of GP88, including GP88's ability to stimulate cell proliferation or to induce tumor growth in experimental animals and in humans. An effective amount of anti-GP88 antibody is administered to an animal, including humans, by various routes. In an alternative embodiment, the anti-GP88 antibody is used as a diagnostic to detect cells which exhibit an altered (increased) expression of GP88 as occurring in diseases such as but not limited to cancers (e.g., breast cancer), and to identify diseased cells whose growth is dependent on GP88 and which will respond to GP88 antagonizing therapy. In yet another embodiment, the anti-GP88 antibody is used to deliver compounds such as cytotoxic factors or antisense oligonucleotides to cells expressing or responsive to GP88. The cytotoxic factors may be attached, linked, or associated with the anti-GP88 antibody.

The antisense oligonucleotides of the invention are also used as a treatment for cancer in cells which exhibit an increased expression of GP88. An effective amount of the antisense oligonucleotide is administered to an animal, including humans, by various routes.

In one embodiment of the invention, GP88 antagonizing agents are used to inhibit or prevent the initiation and/or progression of tumor cells. For example, GP88 antagonizing agents can be used to prevent the occurrence or re-occurrence of breast cancer, other cancers, or other diseases in cells which exhibit an increased expression of GP88 (e.g., neuroblastoma, glioblastoma, astrocytoma, sarcomas, and cancers of the prostate, blood, cerebrospinal fluid, liver, kidney, breast, head and neck, pharynx, thyroid, pancreas, stomach, colon, colorectal, uterus, cervix, bone, bone marrow, testes, brain, neural tissue, ovary, skin, and lung). GP88 antagonizing agents can also be used to restore a normal phenotype to tumor cells overexpressing GP88.

The invention also provides compositions and methods for inducing apoptosis in a tumor cell comprising administering a GP88 antagonist to the cell. Any GP88 antagonist may be used to induce apoptosis (e.g., GP88 antibody or antibody fragment, GP88 antisense nucleic acid, anti-GP88 siRNA, anti-GP88 small molecule, or anti-GP88 receptor antibody). In one embodiment, after administering a GP88 antagonist, the tumor cells undergoing apoptosis are quantified by measuring the level of an apoptotic marker in the tumor cells. For example, elevated levels of Bcl-2 indicate suppression of apoptosis. The apoptotic state of tumor cells can also be determined by measuring cleavage of PARP to its 85 kDa fragment in tumor cells. Apoptosis can be induced in all tumor cell types, including but not limited to, neuroblastoma, glioblastoma, astrocytoma, sarcomas, and cancers of the prostate, blood, cerebrospinal fluid, liver, kidney, breast, head and neck, pharynx, thyroid, pancreas, stomach, colon, colorectal, uterus, cervix, bone, bone marrow, testes, brain, neural tissue, ovary, skin, and lung.

Methods of inducing apoptosis in a tumor comprising co-administering a GP88 antagonist and an anti-estrogen also are provided. In one embodiment, the anti-estrogen is selected from the group consisting of tamoxifen, aromatase inhibitors (e.g., Arimidex®, Femera®), and estrogen-receptor downregulators (e.g., Faslodex®).

The present invention provides methods of determining whether cells are undergoing apoptosis comprising measuring the level of GP88 protein in a first biological sample, measuring the level of GP88 protein in a second biological sample, and determining whether the measured level of GP88 protein in the second biological sample is lower than the level of GP88 protein in the first biological sample by an amount sufficient to indicate the cells are undergoing apoptosis. Such biological samples can be derived from fluids and/or tissues including, but not limited to, prostate, blood, bladder, cerebrospinal fluid, serum, plasma, urine, nipple aspirate, thyroid, head and neck, cervix, liver, kidney, breast, pancreas, stomach, colon, nasopharynx, colorectal, uterus, bone, bone marrow, testes, brain, neural tissue, ovary, skin, and lung tissue.

The present invention also provides methods for targeting GP88 antagonizing reagents to the diseased site by conjugating them to an anti-GP88 antibody or an anti-GP88 receptor antibody.

The accompanying drawings, which are incorporated in and constitute a part of this specification, illustrate embodiments of the invention and, together with the description, serve to explain the principles of the invention.

BRIEF DESCRIPTION OF THE DRAWINGS

FIGS. 1A-1C show the nucleotide (SEQ ID NO: 1) and deduced ammo-acid sequence (SEQ ID NO: 2) of mouse GP88. Peptide regions used as antigens to raise anti-GP88 antibodies K19T and S14R are underlined. The region cloned in the antisense orientation in the pCMV4 mammalian expression vector is indicated between brackets.

FIG. 2A shows the nucleotide sequence (SEQ ID NO: 3) of human GP88 cDNA. Indicated between brackets is the region cloned in the antisense orientation into the pcDNA3 mammalian expression system; and FIG. 2B shows the deduced amino-acid sequence (SEQ ID NO: 4) of human GP88. The E19V region used as antigen to develop anti-human GP88 neutralizing antibody is underlined. It also indicates the region A14R equivalent to the mouse S14R region.

FIG. 3 shows the amino-acid sequence (SEQ ID NO: 2) of mouse GP88 arranged to show the 7 and one-half repeats defined as granulins g, f, B, A, C, D and e (right side). The consensus sequence is shown in SEQ ID NO: 17. This representation shows that the region K19T and S14R used to raise GP88 antibodies for developing anti-GP88 neutralizing antibodies is found between two epithelin/granulin repeats in what is considered a variant region. Indicated on the right hand side is the granulin classification of the repeats according to Bateman et al (6). Granulin B and granulin A are also defined as epithelin 2 and epithelin 1 respectively according to Plowman et al., 1992 (5).

FIG. 4 shows a schematic representation of pCMV4 and a GP88 cDNA clone indicating the restriction sites used to clone GP88 antisense cDNA into the expression vector.

FIG. 6 shows that anti-GP88 antibodies induce apoptosis. Tamoxifen-resistant MCF-7 cells are unable to downregulate Bcl-2. In the present of GP88 antibodies or GP88 antibodies plus tamoxifen, Bcl-2 is downregulated.

DETAILED DESCRIPTION OF THE INVENTION

Figure 5:
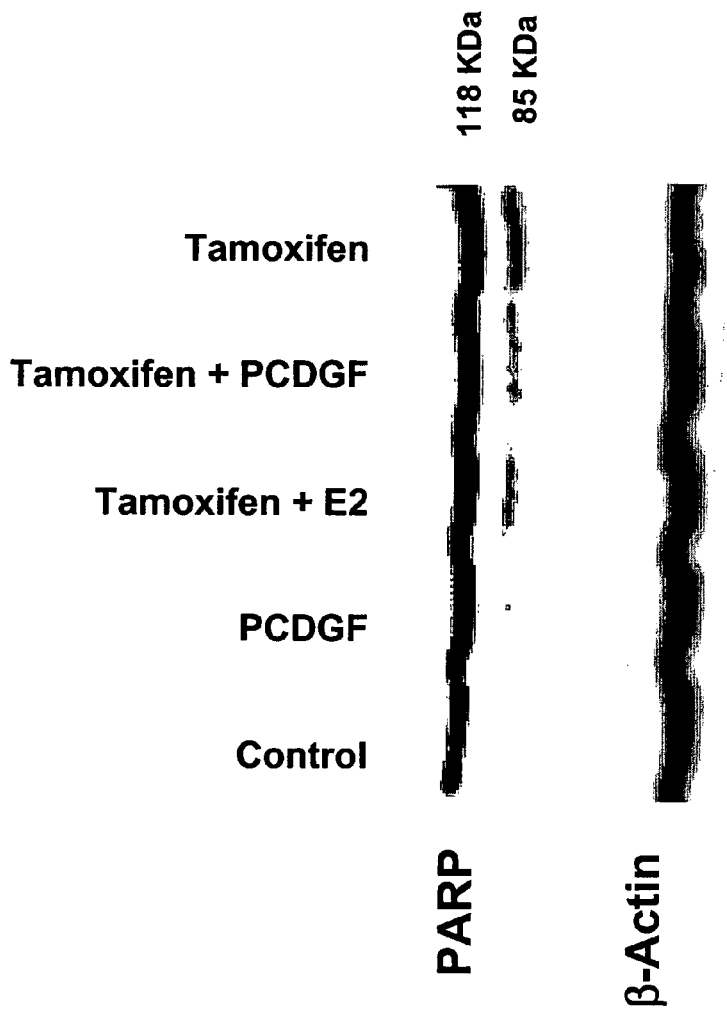
FIG. 5 shows that GP88 inhibits apoptosis in MCF-7 cells in response to tamoxifen. PARP (poly (ADP ribose) polymerase), an apoptosis marker, is cleaved to produce an 85 kDa fragment in the presence of tamoxifen, but not in the presence of GP88 or tamoxifen plus GP88.

Reference will now be made in detail to the presently preferred embodiments of the invention, which, together with the following examples, serve to explain the principles of the invention.

Biological Activity of GP88

The invention relates to GP88 and antitumor and antiviral compositions useful for treating and diagnosing diseases linked to altered (increased) expression of GP88. In addition, this invention is used for treating and diagnosing diseases linked to increased responsiveness to GP88. In accordance with preferred embodiments of the invention, GP88 antagonizing agents (e.g., antibodies, antisense, siRNA, small molecules) can be used to restore sensitivity to the antitumorigenic effects of antiestrogen therapy and induce apoptosis.

Anti-GP88 Antibodies

The invention provides compositions for treating and diagnosing diseases linked to increased expression of GP88 including treatment and diagnosis of diseases linked to increased responsiveness to GP88. The compositions of this invention include anti-GP88 antibodies which neutralize the biological activity of GP88.

The present invention is also directed to an antibody specific for an epitope of GP88 and the use of such antibody to detect the presence or measure the quantity or concentration of GP88 molecule, a functional derivative thereof or a homologue from different animal species in a cell, a cell or tissue extract, culture medium or biological fluid (e.g., whole blood, serum, plasma, lymph, and urine). Moreover, anti-GP88 antibody can be used to target cytotoxic molecules to a specific site.

For use as antigen for development of antibodies, the GP88 protein naturally produced or expressed in recombinant form or functional derivative thereof, preferably having at least 9 amino-acids, is obtained and used to immunize an animal for production of polyclonal or monoclonal antibody. An antibody is said to be capable of binding a molecule if it is capable of reacting with the molecule to thereby bind the molecule to the antibody. The specific reaction is meant to indicate that the antigen will react in a highly selective manner with its corresponding antibody and not with the multitude of other antibodies which may be evoked by other antigens.

The term antibody herein includes but is not limited to human and non-human polyclonal antibodies, human and non-human monoclonal antibodies (mAbs), chimeric antibodies, anti-idiotypic antibodies (anti-IdAb) and humanized antibodies. Polyclonal antibodies are heterogeneous populations of antibody molecules derived either from sera of animals immunized with an antigen or from chicken eggs. Monoclonal antibodies ("mAbs") are substantially homogeneous populations of antibodies to specific antigens. mAbs may be obtained by methods known to those skilled in the art (e.g., U.S. Pat. No. 4,376,110). Such antibodies may be of any immunological class including IgG, IgM, IgE, IgA, IgD and any subclass thereof. The hybridoma producing human and non-human antibodies to GP88 may be cultivated in vitro or in vivo. For production of a large amount of mAbs, in vivo is the presently preferred method of production. Briefly, cells from the individual hybridomas are injected intraperitoneally into pristane primed Balb/c mice or Nude mice to produce ascites fluid containing high concentrations of the desired mAbs. mAbs may be purified from such ascites fluids or from culture supernatants using standard chromatography methods well known to those of skill in the art.

Human monoclonal Ab to human GP88 can be prepared by immunizing transgenic mice expressing human immunoglobulin genes. Hybridoma produced by using lymphocytes from these transgenic animals will produce human immunoglobulin instead of mouse immunoglobulin.

Since most monoclonal antibodies are derived from murine source and other non-human sources, their clinical efficiency may be limited due to the immunogenicity of rodent mAbs administered to humans, weak recruitment of effector function and rapid clearance from serum. To circumvent these problems, the antigen-binding properties of murine antibodies can be conferred to human antibodies through a process called humanization. A humanized antibody contains the amino-acid sequences for the 6 complementarity-determining regions (CDRs) of the parent murine mAb which are grafted onto a human antibody framework. The low content of non-human sequences in humanized antibodies (around 5%) has proven effective in both reducing the immunogenicity and prolonging the serum half life in humans. Methods such as the ones using monovalent phage display and combinatorial library strategy for humanization of monoclonal antibodies are now widely applied to the humanization of a variety of antibodies and are known to people skilled in the art. These humanized antibodies and human antibodies developed with transgenic animals as described above are of great therapeutic use for several diseases including but not limited to cancer.

Hybridoma supernatants and sera are screened for the presence of antibody specific for GP88 by any number of immunoassays including dot blots and standard immunoassays (EIA or ELISA) which are well known in the art. Once a supernatant has been identified as having an antibody of interest, it may be further screened by Western blotting to identify the size of the antigen to which the antibody binds. One of ordinary skill in the art will know how to prepare and screen such hybridomas without undue experimentation in order to obtain a desired polyclonal or mAb.

Chimeric antibodies have different portions derived from different animal species. For example, a chimeric antibody might have a variable region from a murine mAb and a human immunoglobulin constant region. Chimeric antibodies and methods for their production are also known to those skilled in the art.

Accordingly, mAbs generated against GP88 may be used to induce human and non-human anti-IdAbs in suitable animals. Spleen cells from such immunized mice are used to produce hybridomas secreting human or non-human anti-Id mAbs. Further, the anti-Id mAbs can be coupled to a carrier such as Keyhole Limpet Hemocyanin (KLH) or bovine serum albumin (BSA) and used to immunize additional mice. Sera from these mice will contain human or non-human anti-anti-IdAb that have the binding properties of the original mAb specific for a GP88 polypeptide epitope. The anti-Id mAbs thus have their own idiotypic epitopes or idiotypes structurally similar to the epitope being evaluated.

The term antibody is also meant to include both intact molecules as well as fragments thereof such as, for example, Fab and F(ab')2, which are capable of binding to the antigen. Fab and F(ab')2 fragments lack the Fc fragment of intact antibody, clear more rapidly from the circulation and may have less non-specific tissue binding than an intact antibody. Such fragments are typically produced by proteolytic cleavage, using enzymes such as papain (to generate Fab fragments) and pepsin (to generate F(ab')2 fragments). It will be appreciated that Fab and F(ab')2 and other fragments of the antibodies useful in the present invention may be used for the detection or quantitation of GP88, and for treatment of pathological states related to GP88 expression, according to the methods disclosed herein for intact antibody molecules.

According to the present invention, antibodies that neutralize GP88 activity in vitro can be used to neutralize GP88 activity in vivo to treat diseases associated with increased GP88 expression or increased responsiveness to GP88. A subject, preferably a human subject, suffering from a disease associated with increased GP88 expression is treated with an antibody to GP88. Such treatment may be performed in conjunction with other anti-cancer or anti-viral therapy. A typical regimen comprises administration of an effective amount of the antibody specific for GP88 administered over a period of one or several weeks and including between about one and six months. The antibody of the present invention may be administered by any means that achieves its intended purpose. For example, administration may be by various routes including but not limited to subcutaneous, intravenous, intradermal, intramuscular, intraperitoneal and oral. Parenteral administration can be by bolus injection or by gradual perfusion over time. Preparations for parenteral administration include sterile aqueous or non-aqueous solutions, suspensions and emulsions, which may contain auxiliary agents or excipients known in the art. Pharmaceutical compositions such as tablets and capsules can also be prepared according to routine methods. GP88 antagonists can be formulated in any suitable pharmaceutically acceptable carrier (e.g., tablets, pills, injections, infusions, inhalations, transdermal patches, and suppositories). It is understood that the dosage will be dependent upon the age, sex and weight of the recipient, kind of concurrent treatment, if any, frequency of treatment and the nature of the effect desired. The ranges of effective doses provided below are not intended to limit the invention and merely represent preferred dose ranges. However, the most preferred dosage will be tailored to the individual subject as is understood and determinable by one skilled in the art. The total dose required for each treatment may be administered by multiple doses or in a single dose. Effective amounts of antibody are from about 0.01 µg to about 100 mg/kg body weight and preferably from about 10 µg to about 50 mg/kg. Antibody may be administered alone or in conjunction with other therapeutics directed to the same disease.

According to the present invention and concerning the neutralizing antibody, GP88 neutralizing antibodies can be used in all therapeutic cases where it is necessary to inhibit GP88 biological activity, even though there may not necessarily be a change in GP88 expression, including cases where there is an overexpression of GP88 cell surface receptors and this in turn results in an increased biological activity, or where there is an alteration in GP88 signaling pathways or receptors leading to the fact that the signaling pathways are always "turned on." Neutralizing antibodies to growth factor and to growth factor receptors have been successfully used to inhibit the growth of cells whose proliferation is dependent on this growth factor. This has been the case for IGF-I receptor in human breast carcinoma cells and bombesin for lung cancer. The antibody to GP88 can also be used to deliver compounds such as, but not limited to, cytotoxic reagents such as toxins, oncotoxins, mitotoxins and immunotoxins, or antisense oligonucleotides, in order to specifically target them to cells expressing or responsive to GP88.

One region that allows antigen to develop a neutralizing antibody to GP88 is the 19 amino-acid region defined as K19T in the mouse GP88, and E19V in the human GP88 which is not located within the epithelin/granulin 6 kDa repeats but between these repeats, specifically between granulin A (epithelin 1) and granulin C in what is considered a variant region (see FIG. 3). Without wishing to be bound by theory, it is believed that the region important for the biological activity of GP88 lies outside of the epithelin repeats.

The antibodies or fragments of antibodies useful in the present invention may also be used to quantitatively or qualitatively detect the presence of cells which express the GP88 protein. This can be accomplished by immunofluorescence techniques employing a fluorescently labeled antibody (see below) with fluorescent microscopic, flow cytometric, or fluorometric detection. The reaction of antibodies and polypeptides of the present invention may be detected by immunoassay methods well known in the art.

The antibodies of the present invention may be employed histologically as in light microscopy, immunofluorescence or immunoelectron microscopy, for in situ detection of the GP88 protein in tissues samples, biopsies, and biological fluids. In situ detection may be accomplished by removing a histological specimen from a patient and applying the appropriately labeled antibody of the present invention. The antibody (or fragment) is preferably provided by applying or overlaying the labeled antibody (or fragment) to the biological sample. Through the use of such a procedure, it is possible to determine not only the presence of the GP88 protein but also its distribution in the examined tissue or concentration in a biological fluid. Using the present invention, those of ordinary skill in the art will readily perceive that any wide variety of histological methods (such as staining procedures) can be modified in order to achieve such in situ detection.

Assays for GP88 typically comprise incubating a biological sample such as a biological fluid, a tissue extract, freshly harvested or cultured cells or their culture medium in the presence of a detectably labeled antibody capable of identifying the GP88 protein and detecting the antibody by any of a number of techniques well known in the art.

The biological sample may be treated with a solid phase support or carrier such as nitrocellulose or other solid support capable of immobilizing cells or cell particles or soluble proteins. The support may then be washed followed by treatment with the detectably labeled anti-GP88 antibody. This is followed by wash of the support to remove unbound antibody. The amount of bound label on said support may then be detected by conventional means. The term solid phase support refers to any support capable of binding antigen or antibodies such as but not limited to glass, polystyrene polypropylene, nylon, modified cellulose, or polyacrylamide.

The binding activity of a given lot of antibody to the GP88 protein may be determined according to well known methods. Those skilled in the art will be able to determine operative and optimal assay conditions for each determination by employing routine experimentation.

Detection of the GP88 protein or functional derivative thereof and of a specific antibody for the protein may be accomplished by a variety of immunoassays well known in the art such as enzyme linked immunoassays (EIA) or radioimmunoassays (RIA). Such assays are well known in the art and one of skill will readily know how to carry out such assays using the anti-GP88 antibodies and GP88 protein of the present invention.

Such immunoassays are useful to detect and quantitate GP88 protein in serum or other biological fluid as well as in tissues, cells, cell extracts, or biopsies. In a preferred embodiment, the concentration of GP88 is measured in a tissue specimen as a means for diagnosing cancer or other disease associated with increased expression of GP88. In another preferred embodiment, the concentration of GP88 in a biological fluid sample is used to determine if a patient is likely to be responsive, or is responding to, anti-tumorigenic therapy.

The presence of certain types of cancers (e.g., breast cancer) and the degree of malignancy are said to be "proportional" to an increase in the level of the GP88 protein. The term "proportional" as used herein is not intended to be limited to a linear or constant relationship between the level of protein and the malignant properties of the cancer. The term "proportional" as used herein, is intended to indicate that an increased level of GP88 protein is related to appearance, recurrence or display of malignant properties of a cancer or other disease associated with increased expression of GP88 at ranges of concentration of the protein that can be readily determined by one skilled in the art.

Another embodiment of the invention relates to evaluating the efficacy of anti-cancer or anti-viral drug or agent by measuring the ability of the drug or agent to inhibit the expression or production of GP88. The antibodies of the present invention are useful in a method for evaluating anti-cancer or anti-viral drugs in that they can be employed to determine the amount of the GP88 protein in one of the above-mentioned immunoassays. Alternatively, the amount of the GP88 protein produced is measured by bioassay (cell proliferation assay) as described herein. The bioassay and immunoassay can be used in combination for a more precise assessment.

An additional embodiment is directed to an assay for diagnosing cancers or other diseases associated with an increase in GP88 expression based on measuring in a tissue or biological fluid the amount of mRNA sequences present that encode GP88 or a functional derivative thereof, preferably using an RNA-DNA hybridization assay. The presence of certain cancers and the degree of malignancy is proportional to the amount of such mRNA present. For such assays the source of mRNA will be biopsies and surrounding tissues. The preferred technique for measuring the amount of mRNA is a hybridization assay using DNA of complementarity base sequence.

Another related embodiment is directed to an assay for diagnosing cancers or other diseases associated with an increase in GP88 responsiveness based on measuring on a tissue biopsy whether treatment with anti-GP88 neutralizing antibody will inhibit its growth or other biological activity.

Another related embodiment is a method for measuring the efficacy of anti-cancer or anti-viral drug or agent which comprises the steps of measuring the agent's effect on inhibiting the expression of mRNA for GP88. Similarly such method can be used to identify or evaluate the efficacy of GP88 antagonizing agents by measuring the ability of said agent to inhibit the production of GP88 mRNA.

Nucleic acid detection assays, especially hybridization assays, can be based on any characteristic of the nucleic acid molecule such as its size, sequence, or susceptibility to digestion by restriction endonucleases. The sensitivity of such assays can be increased by altering the manner in which detection is reported or signaled to the observer. A wide variety of labels have been extensively developed and used by those of ordinary skill in the art, including enzymatic, radioisotopic, fluorescent, chemical labels and modified bases.

One method for overcoming the sensitivity limitation of a nucleic acid for detection is to selectively amplify the nucleic acid prior to performing the assay. This method has been referred as the "polymerase chain reaction" or PCR (U.S. Pat. No. 4,683,202 and 4,582,788). The PCR reaction provides a method for selectively increasing the concentration of a particular nucleic acid sequence even when that sequence has not been previously purified and is present only in a single copy in a particular sample.

Restoration of Sensitivity To Antiestrogen Therapy And Cytotoxic Therapy

Tumors progress through various stages of growth and maturation leading to increased mobility of the tumor through the body. Therefore, tumor cells can be targeted at several stages during the progression of tumor growth and maturation. For example, GP88 antagonists inhibit tumor cell growth and proliferation. For example, GP88 induces expression of cyclin D1, a cell cycle regulatory protein involved in the growth and proliferation of tumor cells. As shown in FIG. 11, anti-GP88 antibodies inhibit cyclin D1 expression. Lanes 1 and 2 of FIG. 11 show that anti-GP88 antibody 5B4 inhibits the expression of cyclin D1. Lanes 3 and 4 show that GP88 stimulates cyclin D1 expression. Lanes 5 and 6 demonstrate that anti-GP88 antibody 5B4 blocks induction of cyclin D1 by GP88.

A preferred embodiment of the invention provides a method for restoring sensitivity of tumor cells to antiestrogen therapy, comprising contacting a tumor cell that is nonsensitive to antitumorigenic effects of antiestrogen therapy with a GP88 antagonist in an amount sufficient to restore sensitivity to the antitumorigenic effects of antiestrogen therapy. In one embodiment, the term "restoring sensitivity" refers to increasing the responsiveness of a treated tumor cell to the antitumorigenic effects of antiestrogen therapy. For example, a tumor cell that does not respond to antiestrogen therapy (i.e., continues to grown in an uncontrolled manner), responds to antiestrogen therapy (i.e., is growth inhibited, undergoes apoptosis, etc.) after being contacted with a GP88 antagonist.

The GP88 antagonists or GP88 antagonizing agents include, but are not limited to, anti-GP88 antibodies or antibody fragments, anti-GP88 receptor antibodies, anti-GP88 small molecules, anti-GP88 antisense nucleic acids, and siRNA. GP88 antagonists can prevent tumor formation and growth of any tumor or cancer type, including but not limited to, prostate, head and neck, nasopharynx, thyroid, pancreas, bladder, cervix, colorectal, blood, liver, kidney, breast, bone, bone marrow, testes, ovaries, brain, neural, colon, and lung tumors.

Figure 9:
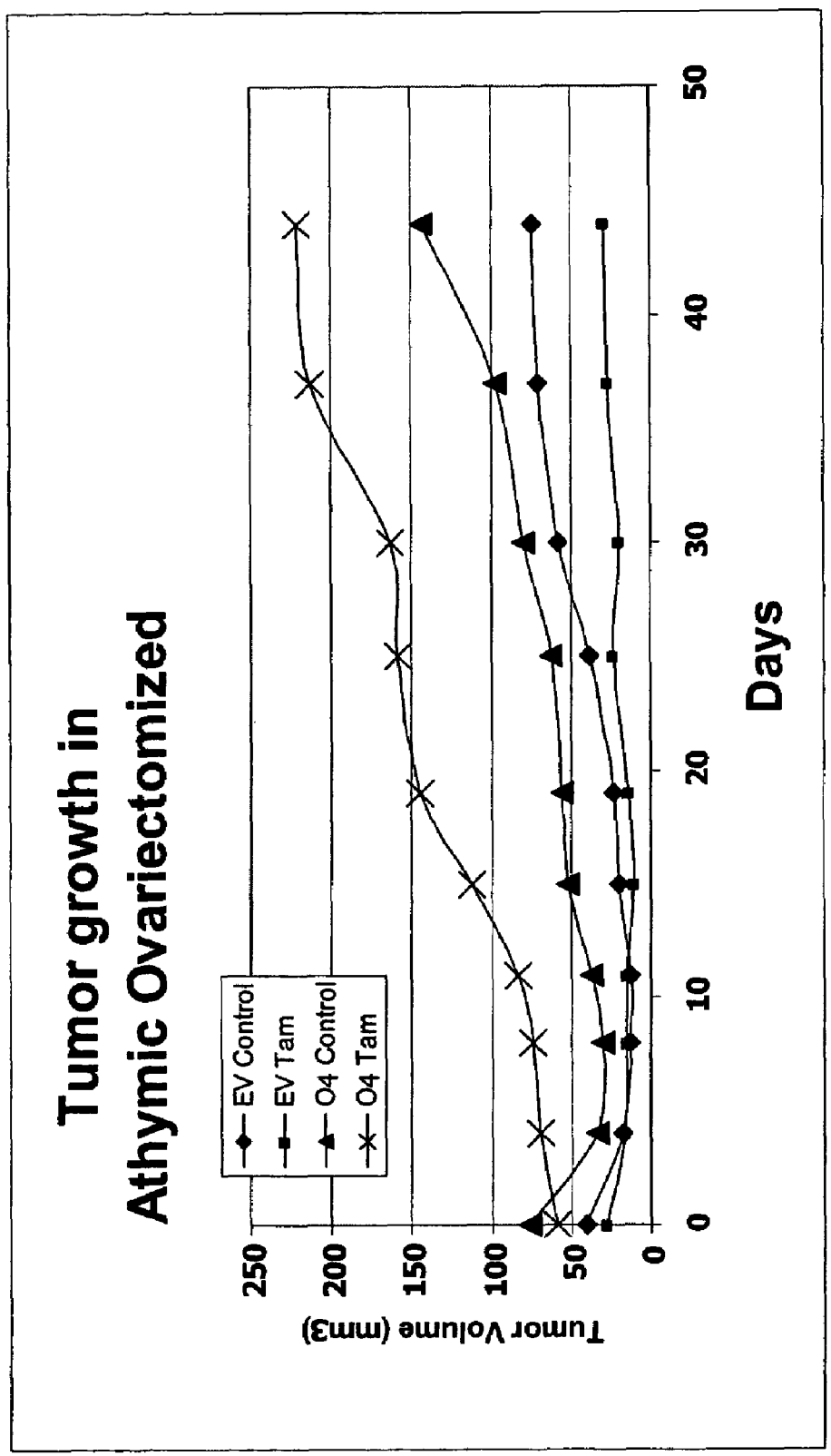
FIG. 9 shows that tamoxifen can induce an increase in tumor volume in GP88 overexpressing cells (O4 cells) in vivo. Thus, treatment with tamoxifen may pose a risk of promoting tumor growth in tumors in which GP88 levels are elevated.

In one embodiment, sensitivity of tumor cells to effects of antiestrogen therapy can be increased by inducing apoptosis. Apoptosis can be induced by contacting an anti-estrogen and GP88 antagonist with a tumor cell. Anti-estrogen therapy relates to administration of anti-estrogens for the purpose of preventing or treating tumor growth. As discussed above, anti-estrogens such as tamoxifen inhibit tumor growth, in part, by inducing apoptosis. However, as shown in FIG. 9, tamoxifen alone may actually stimulate tumor growth in vivo in cells overexpressing GP88. Thus, treatment of patients having high levels of GP88 with anti-estrogens alone may be counterproductive.

Treatment of tumors overexpressing GP88 with both anti-estrogens and anti-GP88 antibodies can induce apoptosis and eliminate the potential growth stimulating properties of anti-estrogen treatment on GP88 overexpressing cells. Examples of anti-estrogens include tamoxifen citrate ("tamoxifen"), a nonsteroidal anti-estrogen commonly prescribed to patients suffering from breast cancer that has demonstrated potent anti-estrogenic and antineoplastic properties. (See U.S. Pat. No. 4,536,516), raloxifene, aromatase inhibitors (e.g., Arimidex® (anastrozole), Femera®, letrozole), and estrogen receptor down-regulators (e.g., Faslodex®).

Tamoxifen-induced apoptosis is blocked in tumor cells overexpressing GP88. FIG. 5 is a western blot measuring the level of the PARP cleavage product (85 kDa band) in MCF-7 breast carcinoma cells treated with tamoxifen, tamoxifen+GP88, tamoxifen+estradiol, GP88, and a control. As shown in FIG. 5, tamoxifen treatment induced apoptosis of MCF-7 cells. The 85 kDa PARP cleavage product was significantly increased in the "Tamoxifen" labeled lane, indicating apoptosis. Tamoxifen-induced apoptosis was blocked by treatment with estradiol, a compound known to block tamoxifen-induced apoptosis, as shown by the decrease in the 85 kDa band in the lane labeled "Tamoxifen+estradiol." Tamoxifen-induced apoptosis was blocked by treatment with GP88 to the same extent as treatment by estradiol. The lane labeled "Tamoxifen+GP88" shows a significant decrease in the PARP cleavage product compared to the "Tamoxifen" lane. FIG. 5 shows that GP88 blocks tamoxifen-induced apoptosis in tumor cells.

Additional embodiments of the invention are directed to compositions and methods of inducing apoptosis. Apoptosis, also known as programmed cell death, is an essential component of the growth regulatory mechanism of a cell. For example, apoptosis is a mechanism for ridding the body of damaged cells (e.g., viral infected cells, cells with DNA damage). Cells undergoing apoptosis are typically smaller than normal cells and have highly condensed nuclei. Apoptotic cells are marked for clearance by the immune system.

Deficient regulation of apoptosis can cause uncontrolled cell growth and tumorigenicity. Oncogenes can be activated by DNA damage. Under normal apoptotic conditions, the body would clear the damaged cell. Under abnormal conditions, apoptosis does not occur and the damaged cell grows and proliferates leading to tumorigenesis. For example, p53 normally functions to induce apoptosis. However, the oncogenic form of p53 blocks induction of apoptosis leading to uncontrolled cell growth. Unregulated cell survival contributes to diseases such as cancer, autoimmune diseases, and inflammatory diseases. As discussed above, the Bcl-2 gene encodes a protein capable of blocking apoptosis. Overexpression of Bcl-2 indicates that apoptosis is blocked and the cell will not undergo programmed cell death.

The present invention provides methods and compositions for restoring sensitivity to the antitumorigenic effects of cytotoxic or chemotherapeutic agents. For example, GP88 antagonists (e.g., anti-GP88 antibodies, GP88 antisense nucleic acids, siRNA, and small molecules, etc.) can be administered to patients who develop resistance to the antitumorigenic effects of cytoxic agents (e.g., Altretamine, Bleomycin, Busulphan, Calcium Folinate, Capecitabine, Carboplatin, Carmustine, Chlorambucil, Cisplatin, Cladribine, Crisantaspase, Cyclophosphamide, Cytarabine, Dacarbazine, Dactinomycin, Daunorubicin, Docetaxel, Doxorubicin, Epirubicin, Etoposide, Fludarabine, Fluorouracil, Gemcitabine, Hydroxyurea, Idarubicin, Ifosfamide, Irinotecan, Liposomal doxorubicin, Lomustine, Melphalan, Mercaptopurine, Methotrexate, Mitomycin, Mitoxantrone, Oxaliplatin, Paclitaxel, Pentostatin, Procarbazine, Raltitrexed, Streptozocin, Tegafur-uracil, Temozolomide, Thiotepa, Tioguanine/Thioguanine, Topotecan, Treosulfan, Vinblastine, Vincristine, Vindesine, and Vinorelbine). Sensitivity and responsiveness to cytotoxic and/or chemotherapeutic agents and combinations thereof can be restored.

In another embodiment of the invention, GP88 antagonists can be co-administered with an antiestrogen and/or a cytotoxic compound to a tumor cell. For example, an anti-GP88 antibody can be co-administered to a tumor cell with tamoxifen to restore sensitivity to the antitumorigenic effects of tamoxifen or to prevent development of tamoxifen resistance. In another embodiment, the GP88 antagonist can be administered sequentially with an antiestrogen and/or a cytotoxic compound. Thus, GP88 antagonist can be administered either before or after administration of the antiestrogen or cytotoxic compound.

The present invention also provides methods of inducing apoptosis comprising administering a GP88 antagonist to a tumor cell. Apoptosis can be induced in all tumor cell types including, but not limited to, neuroblastoma, glioblastoma, astrocytoma, sarcomas, and cancers of the prostate, blood, cerebrospinal fluid, liver, kidney, breast, head and neck, pharynx, thyroid, pancreas, stomach, colon, colorectal, uterus, cervix, bone, bone marrow, testes, brain, neural tissue, ovary, skin, and lung. Apoptosis can be detected in tumor cells by a variety of techniques including, but not limited to for example, detection of Bcl-2 levels or detection of the PARP cleavage product, DNA ladder, and production of apoptotic cells. PARP or poly(ADP-ribose) polymerase is a nuclear binding protein that detects DNA strand breaks and participates in DNA repair. Cleavage of PARP is a hallmark of caspases-dependent apoptosis. When apoptosis takes place, the 116 kDa intact PARP is cleaved in two fragments, 85 kDa and 25 kDa. Detection of intact and cleaved forms of PARP by Western Blot analysis with anti-PARP antibody has been established as an apoptosis assay. Duriez et al., Biochem Cell Biol. 75: 337-49, 1997.

Apoptosis is controlled by the ratio of apoptotic to anti-apoptotic factors, particularly Bcl-2, bcl-xl and bax. Previous reports have suggested that Bcl-2 expression was down-regulated by tamoxifen treatment leading to activation of apoptosis in MCF-7 cells and in tissues from patients treated with tamoxifen. Zhang et al., Clin. Cancer Res. 5: 2971-7, 1999; Cameron et al., Eur. J. Cancer 36: 845-51, 2000. Alteration of Bcl-2 expression levels changes the bax:Bcl-2 ratio and alters susceptibility to apoptosis. O4 cells are MCF-7 cells transformed with a GP88 expression construct to overexpress GP88. Serrero et al., Proc. Natl. Acad. Sci.

U.S.A. 97: 3993-8, 2000. As shown in FIG. 6, tamoxifen induced down-regulation of Bcl-2 transcript in MCF-7 cells at all concentrations tested indicating that tamoxifen induces apoptosis. In contrast, tamoxifen failed to down regulate Bcl-2 in O4 cells even at elevated doses.

Tamoxifen-resistant MCF-7 cells are unable to down-regulate Bcl-2 as shown in FIG. 6. However, the addition of anti-GP88 antibodies to tamoxifen-resistant MCF-7 cells restores apoptosis as indicated by the down-regulation of Bcl-2. (FIG. 6). Thus, GP88 antagonists restore the ability of tamoxifen to induce apoptosis in tamoxifen-resistant cells.

Figure 7:
FIG. 7 also shows that anti-GP88 antibodies induce apoptosis. O4 cells (overexpressing GP88) are unable to cleave PARP. In the presence of anti-GP88 antibodies or anti-GP88 antibodies plus tamoxifen, PARP is cleaved, indicating induction of apoptosis.

Anti-GP88 antibodies also induce apoptosis in O4 cells (GP88-overexpressing, tamoxifen-resistant MCF-7 cells). As shown in FIG. 7, the PARP cleavage product is increased in O4 cells treated with 5B4 antibody (5B4) or 5B4 plus tamoxifen (5B4+T) indicating that treatment of the cells with anti-GP88 antibody induced apoptosis.

Figure 8:
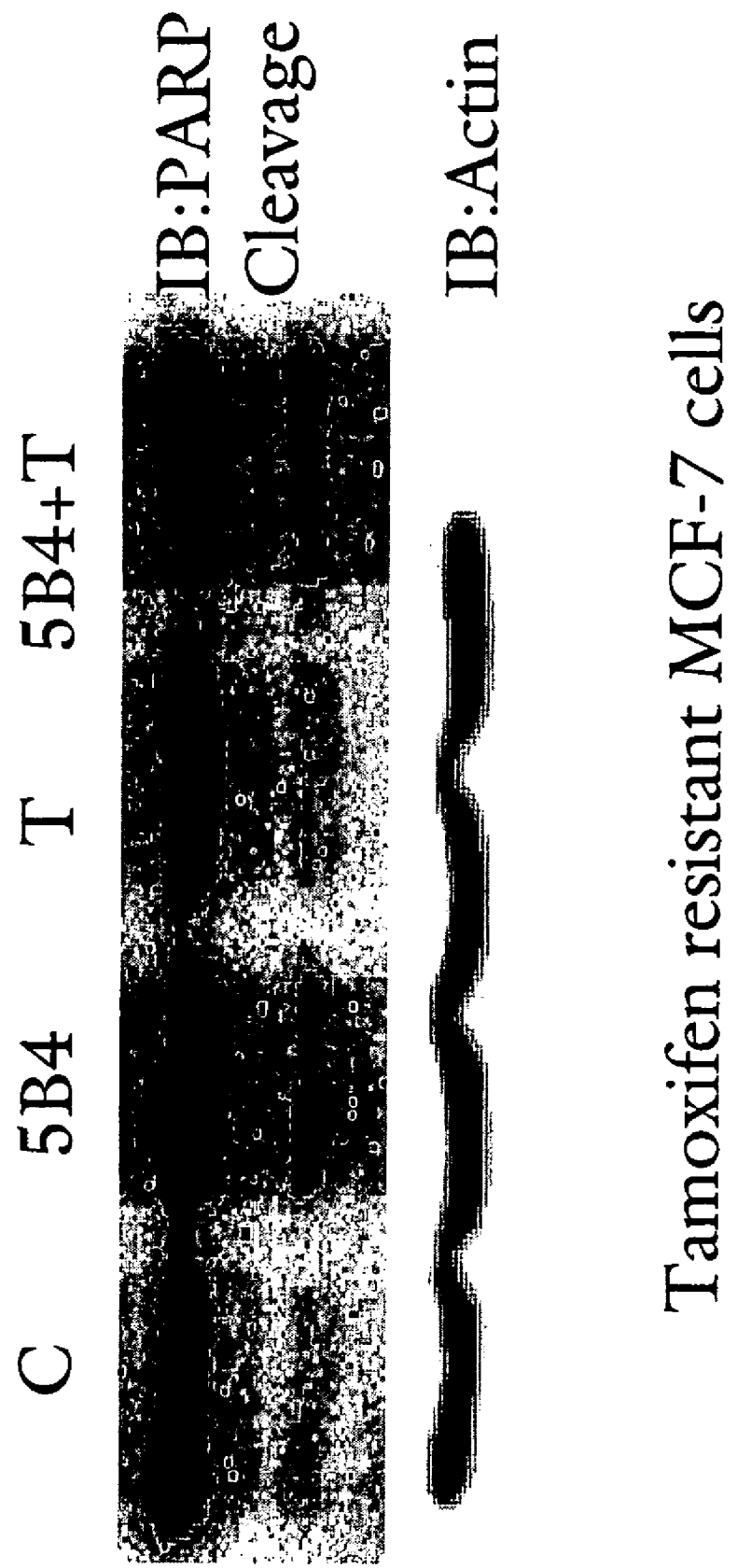
FIG. 8 also shows that anti-GP88 antibodies induce apoptosis. Tamoxifen-resistant MCF-7 cells are unable to cleave PARP. In the presence of anti-GP88 antibodies or anti-GP88 antibodies plus tamoxifen, PARP is cleaved, indicating induction of apoptosis.

Treatment of tamoxifen resistant MCF-7 cells with anti-GP88 antibodies also induces apoptosis. As shown in FIG. 8, addition of anti-GP88 antibody 5B4 alone or in combination with tamoxifen results in cleavage of PARP while treatment with tamoxifen alone does not cleave PARP.

FIG. 9 shows the effect of tamoxifen on the growth of MCF-7 cells and O4 cells in ovariectomized nude mice. Athymic ovariectomized female nude mice were implanted with an estradiol pellet one day before being injected (S.C) with either MCF-7 cells or O4 cells. After 10 days when the tumors were visible, the mice received either a placebo pellet or tamoxifen pellet. Tumor growth was monitored for 45 days. At the end of the experiments, mice were euthanized and the tumors were excised and evaluated. As shown in FIG. 9, tumor volume in mice with tumors induced by O4 cells (GP88 overexpressing cells) and treated with tamoxifen increased from 50 mm$^3$ to about 225 mm$^3$ after 45 days. In contrast, tumor volume in mice with tumor induced by O4 cells and untreated with tamoxifen increased from 75 mm$^3$ to 150 mm$^3$ in 45 days. Tamoxifen treatment of tumors overexpressing GP88 increased tumor volume more than 4 times while tumor volume of untreated GP88 overexpressing tumors increased by 2 times.

Thus, GP88 antagonizing agents (e.g., anti-GP88 antibodies, GP88 antisense nucleic acids, siRNA, anti-GP88 small molecules, etc.) can be administered to tumor cells and restore the antitumorigenic effects of antiestrogen therapy, for example, by inducing apoptosis.

GP88 antibodies suitable for restoring sensitivity to antiestrogen therapy and cytotoxic therapy, and in other preferred compositions methods of the invention (e.g., inducing apoptosis, etc.) have been deposited with the American Type Culture Collection (ATCC), 10801 University Blvd., Manassas, Va. 20110-2209, and may be produced from hybridoma cell lines, including, but not limited to, 6B3 hybridoma cell line (ATCC Accession Number PTA-5262), 6B2 hybridoma cell line (ATCC Accession Number PTA-5261), 6C12 hybridoma cell line (ATCC Accession Number PTA-5597), 5B4 hybridoma cell line (ATCC Accession Number PTA-5260), 5G6 hybridoma cell line (ATCC Accession Number PTA-5595), 4D1 hybridoma cell line (ATCC Accession Number PTA-5593), 3F8 hybridoma cell line (ATCC Accession Number PTA-5591), 3F5 hybridoma cell line (ATCC Accession Number PTA-5259), 3F4 hybridoma cell line (ATCC Accession Number PTA-5590), 3G2 (ATCC Accession Number PTA-5592), and 2A5 hybridoma cell line (ATCC Accession Number PTA-5589).

In another embodiment of the invention, anti-GP88 receptor antibodies, including antibodies produced from hybridoma cell lines including, but not limited to, 6G8 hybridoma cell line (ATCC Accession Number PTA-5263) and 5A8 hybridoma cell line (ATCC Accession Number PTA-5594) can be used to restore sensitivity to the antitumorigenic effects of antiestrogen therapy and cytotoxic therapy and induce apoptosis in tumor cells.

Each of these hybridoma cell lines have been deposited with the American Type Culture Collection (ATCC), 10801 University Blvd., Manassas, Va. 20110-2209. 3F5 hybridoma cell line (ATCC Accession Number PTA-5259), 6B3 hybridoma cell line (ATCC Accession Number PTA-5262), 6B2 hybridoma cell line (ATCC Accession Number PTA-5261), 6G8 hybridoma cell line (ATCC Accession Number PTA-5263) and 5B4 hybridoma cell line (ATCC Accession Number PTA-5260) were deposited on Jun. 12, 2003; 5A8 hybridoma cell line (ATCC Accession Number PTA-5594), 5G6 hybridoma cell line (ATCC Accession Number PTA-5595), 4D1 hybridoma cell line (ATCC Accession Number PTA-5593), 3F8 hybridoma cell line (ATCC Accession Number PTA-5591), 3F4 hybridoma cell line (ATCC Accession Number PTA-5590), 3G2 (ATCC Accession Number PTA-5592), 6C12 hybridoma cell line (ATCC Accession Number PTA-5597), and 2A5 hybridoma cell line (ATCC Accession Number PTA-5589) were deposited on Oct. 17, 2003.

Anti-GP88 antibodies and anti-GP88 receptor antibodies (collectively "GP88 antagonist antibodies") can be provided to cells both in vitro and in vivo. For in vitro applications, GP88 antagonist antibodies can be added to cell culture medium at concentrations typically ranging from 0.01 ng to about 100 mg/ml of cell culture media and preferably from about 10 ng to about 50 mg/ml. Antibody may be administered alone or in conjunction with other therapeutics directed to the same disease. Cells can also be transfected with DNA or RNA encoding GP88 antagonist antibodies or antibody fragments or vectors containing such DNA or RNA sequences. Transfected cells can be induced to make GP88 antagonist antibodies or antibody fragments using any suitable technique (e.g., inducible promoter, and multiple plasmid copies).

GP88 antagonist antibody compositions can also be administered to cells using ex vivo techniques. Tumorigenic or normal cells can be removed from a subject (e.g., human or other mammal) and grown in culture. The cells can then be transfected with DNA or RNA encoding GP88 antagonist antibodies and induced to produce GP88 antagonist antibodies. The transfected cells can then be re-introduced into the subject to produce GP88 antagonist antibodies or antibody fragments and inhibit the activity of GP88, reduce tumor cell proliferation, and reduce tumor volume.

For in vivo applications, GP88 antagonist antibody compositions can be provided to a subject by a variety of administration routes and dosage forms. A subject suffering from disease associated with increased GP88 expression may be treated with a GP88 antagonist antibody or fragment. Alternatively, a subject's cells are transfected with a polynucleotide encoding a GP88 antagonist antibody or fragment. A typical regimen comprises administering of an effective amount of the GP88 antagonist antibody over a period of one week to about six months.

The GP88 antagonists of the present invention may be administered by various routes, including, but not limited to, subcutaneous, intravenous, intradermal, intramuscular, intraperitoneal and oral. Parenteral administration can be by bolus injection or by gradual perfusion over time. Preparations for parenteral administration include sterile aqueous or non-aqueous solutions, suspensions and emulsions, which may contain auxiliary agents or excipients known in the art.

Pharmaceutical compositions such as tablets and capsules can also be prepared. Pharmaceutically acceptable carriers (e.g., tablets, pills, injections, infusions, inhalations, transdermal patches, and suppositories) can be used to administer GP88 antagonists to a patient. The pharmaceutical compositions of the invention comprise GP88 antagonists and can include antiestrogens and/or cytotoxic compounds.

It is understood that the dosage will be dependent upon the age, sex and weight of the recipient, kind of concurrent treatment, if any, frequency of treatment and the nature of the effect desired. The ranges of effective doses provided below are not intended to limit the invention and merely represent illustrative dose ranges. However, the most preferred dosage will be tailored to the individual subject as is understood and determinable by one of ordinary skill in the art given the teachings herein. The total dose required for each treatment may be administered by multiple doses or in a single dose. Effective amounts of antibody are typically from about 0.01 μg to about 100 mg/kg body weight and preferably from about 10 μg to about 50 mg/kg. Antibody may be administered alone or in conjunction with other therapeutics directed to the same disease.

The present invention also provides methods for determining responsiveness to GP88 antagonist treatment comprising measuring the level of GP88 protein in a first biological sample; measuring the level of GP88 protein in a second biological sample; and determining whether the measured level of GP88 protein in the second biological sample is lower than the level of GP88 protein in the first biological sample by an amount sufficient to indicate the cells are responding to GP88 antagonist treatment. The term "responding to GP88 antagonist treatment" refers to preventing, suppressing, and/or decreasing cell growth or tumor cell growth.

The level of GP88 in a first or initial biological sample can be measured and compared to the level of GP88 in a second tumor biological sample taken at a different time. For example, biological samples or biopsies can be taken at regular intervals and the measured concentration of GP88 in subsequent samples can be compared to the GP88 level in the initial sample. A decrease in the level of GP88 in the tumor samples over time is indicative that the cells responding to GP88 antagonist treatment.

GP88 Expression Inhibitors

This invention also provides GP88 expression inhibitors (e.g., antisense components, and siRNA). The term antisense component corresponds to an RNA sequence as well as a DNA sequence coding therefor, which is sufficiently complementary to a particular mRNA molecule, for which the antisense RNA is specific, to cause molecular hybridization between the antisense RNA and the mRNA such that translation of the mRNA is inhibited. Such hybridization can occur under in vivo conditions. The action of the antisense RNA results in specific inhibition of gene expression in the cells. For example, antisense components can block translation of an mRNA and/or block or prevent splicing of mRNA. Antisense molecules can also be directed to bind to introns which are less conserved between species resulting in greater specificity (e.g., inhibiting expression of a gene product of one species but not its homologue in another species).

siRNA are double-stranded (ds) RNA molecules that inhibit gene expression by forming a complex with a target nucleic acid. One strand, called the sense strand is complementary to the target nucleic acid (e.g., messenger RNA ("mRNA")) while the second strand is complementary to the sense strand. Fire et al., Nature, 391(6669):806-811 (1998). siRNA or RNAi can be used to inhibit gene expression in a variety of species (e.g., C. elegans Id. and Drosophila (Kennerdell and Carthew, Cell (1998) 95:1017-1026; Misquitta and Patterson, PNAS (1999) 96:1451-1456)). In one embodiment, dsRNA used as siRNA can be generated by transcription in vivo. Alternatively, dsRNA can be generated in vitro using the polymerase chain reaction (PCR) or other techniques (e.g., Promega Large Scale RNA Production System (Madison, Wis.)) according to standard and other protocols. In another embodiment, complementary sense and antisense RNA strands can be derived from the sequence of the target gene (e.g., GP88) and can be synthesized. The resulting sense and antisense RNAs can be annealed in a buffer and administered to an animal or used in cell culture experiments. See e.g., Timmons and Fire, Nature (1998) 395:854; Montgomery et al., PNAS (1998) 95:15502-15507; Tabara et al., Science (1998) 282:430-431.

The double-stranded siRNA forms a complex with and cleaves the target mRNA, resulting in destruction of the target RNA. Id. The double-stranded siRNA is incorporated into a complex called RNA-induced silencing complex or RISC. Kim et al., J. Korean Med Sci 18:309-18 (2003). RNA helicase catalyzes the destruction of one of the strands of the siRNA activating the RISC complex resulting in the targeting and destruction of the target RNA molecule. Id. siRNA have high specificity for their target genes and can inhibit gene expression by 90% in most genes. Id.

Preferably, siRNA directed to GP88 interfere with the function of GP88 mRNA. These may be directed against any portion of the GP88, preferably of at least about 20 nucleotides in length. siRNA directed against GP88, in accordance with the invention, are capable of inhibiting tumor cell growth, preventing tumor cell growth, inducing tumor regression, and inducing apoptosis.

siRNA directed against GP88 can be targeted against any suitable sequence. siRNA can be made to target any portion of the GP88 nucleotide sequence. After binding to a portion of the GP88 nucleotide sequence, the GP88 nucleic acid is marked for destruction. In one embodiment, the siRNA is generated from a single stranded oligonucleotide having the following sequence: 5' AGGTTGATGCCCACTGCTCTG 3' (SEQ ID NO: 5) (siRNA Sequence 1). siRNA Sequence 1 targets the human GP88 nucleotide region beginning at nucleotide position 203 (FIG. 2A). siRNA targeting the human GP88 sequence beginning at position 223 of GP88 has the following sequence: GAGCAGUGGGCAUCAAC-CUGG (SEQ ID NO: 6) (siRNA Sequence 2). siRNA Sequence 3 (5' AGATCAGGTAACAACTCCGTG 3') (SEQ ID NO: 7) targets the human GP88 sequence beginning at nucleotide 342. siRNA Sequence 4 (5' GGACACTTCTGC-CATGATAAC 3') (SEQ ID NO: 8) targets the human GP88 sequence beginning at nucleotide 1569.

In one embodiment, the siRNA sequences can be made into double stranded siRNA sequences according to methods well known in the art. It is understood that siRNA can be generated to target any suitable region of the GP88 nucleotide sequence from a variety of species (human, mouse, porcine, canine, etc.). Nucleotide substitutions, deletions, reversions, and mutations can be introduced into the siRNA sequences without altering the function of the siRNA to target the GP88 nucleic acid (e.g., mRNA) for destruction.

Transfection of tumor cells with DNA antisense or siRNA to the GP88 cDNA inhibits endogenous GP88 expression and inhibits tumorigenicity of the transfected cells. This antisense DNA should have sufficient complementarity, about 18-30 nucleotides in length, to the GP88 gene so that the antisense RNA can hybridize to the GP88 gene (or mRNA) and inhibit GP88 gene expression regardless of whether the action is at the level of splicing, transcription, or translation. The degree of inhibition is readily discernible to one skilled in the art without undue experimentation given the teachings herein and preferably is sufficient to inhibit the growth of cells whose proliferation is dependent on the expression of GP88. One of ordinary skill in the art will recognize that the antisense RNA approach is but a number of mechanisms which can be employed to block specific gene expression.

The antisense components of the present invention may be hybridizable to any of several portions of the target GP88 cDNA, including the coding sequence, 3' or 5' untranslated regions, or other intronic sequences, or to GP88 mRNA. As is readily discernible by one of ordinary skill in the art, the minimal amount of homology required by the present invention is that sufficient to result in hybridization to the GP88 DNA or mRNA and in inhibition of transcription of the DNA, or translation or function of the mRNA, preferably without affecting the function of other mRNA molecules and the expression of other unrelated genes.

Antisense RNA may be delivered to a cell by transformation or transfection via a vector, including retroviral vectors and plasmids, into which has been placed DNA encoding the antisense RNA with the appropriate regulatory sequences including a promoter to result in expression of the antisense RNA in a host cell. Stable transfection of various antisense expression vectors containing GP88 cDNA fragments in the antisense orientation have been performed. One can also deliver antisense components to cells using a retroviral vector. Delivery can also be achieved by, for example, liposomes or nucleofection.

For purposes of in vivo therapy, the currently preferred method is to use antisense oligonucleotides, instead of performing stable transfection of an antisense cDNA fragment constructed into an expression vector. Antisense oligonucleotides having a size of 15-30 bases in length and with sequences hybridizable to any of several portions of the target GP88 cDNA, including the coding sequence, 3' or 5' untranslated regions, or other intronic sequences, or to GP88 mRNA are preferred. Sequences for the antisense oligonucleotides to GP88 are preferably selected as being the ones that have the most potent antisense effects. Factors that govern a target site for the antisense oligonucleotide sequence are related to the length of the oligonucleotide, binding affinity, and accessibility of the target sequence. Sequences may be screened in vitro for potency of their antisense activity by measuring inhibition of GP88 protein translation and GP88 related phenotype, e.g., inhibition of cell proliferation in cells in culture. In general, it is known that most regions of the RNA (5' and 3' untranslated regions, AUG initiation, coding, splice junctions and introns) can be targeted using antisense oligonucleotides.

The preferred GP88 antisense oligonucleotides are those oligonucleotides which are stable, have a high resilience to nucleases (enzymes that could potentially degrade oligonucleotides), possess suitable pharmacokinetics to allow them to traffic to disease tissue at non-toxic doses, and have the ability to cross through plasma membranes.

Phosphorothioate antisense oligonucleotides may be used. Modifications of the phosphodiester linkage as well as of the heterocycle or the sugar may provide an increase in efficiency. With respect to modification of the phosphodiester linkage, phophorothioate may be used. An N3'-P5' phosphoramidate linkage has been described as stabilizing oligonucleotides to nucleases and increasing the binding to RNA. Peptide nucleic acid (PNA) linkage is a complete replacement of the ribose and phosphodiester backbone and is stable to nucleases, increases the binding affinity to RNA, and does not allow cleavage by RNAse H. Its basic structure is also amenable to modifications that may allow its optimization as an antisense component. With respect to modifications of the heterocycle, certain heterocycle modifications have proven to augment antisense effects without interfering with RNAse H activity. An example of such modification is C-5 thiazole modification. Modification of the sugar may also be considered. 2'-O-propyl and 2'-methoxyethoxy ribose modifications stabilize oligonucleotides to nucleases in cell culture and in vivo. Cell culture and in vivo tumor experiments using these types of oligonucleotides targeted to c-raf-1 resulted in enhanced potency.

The delivery route will be the one that provides the best antisense effect as measured according to the criteria described above. In vitro cell culture assays and in vivo tumor growth assays using antisense oligonucleotides have shown that delivery mediated by cationic liposomes, by retroviral vectors and direct delivery are efficient. Another possible delivery mode is targeting using antibody to cell surface markers for the tumor cells. Antibody to GP88 or to its receptor may serve this purpose.

Recombinant GP88

The present invention is also directed to DNA expression systems for expressing a recombinant GP88 polypeptide or a functional derivative thereof substantially free of other mammalian DNA sequences. Such DNA may be double or single stranded. The DNA sequence should preferably have about 20 or more nucleotides to allow hybridization to another polynucleotide. In order to achieve higher specificity of hybridization, characterized by the absence of hybridization to sequences other than those encoding the GP88 protein or a homologue or functional derivative thereof, a length of at least 50 nucleotides is preferred.

The present invention is also directed to the above DNA molecules, expressible vehicles or vectors as well as hosts transfected or transformed with the vehicles and capable of expressing the polypeptide. Such hosts may be prokaryotic, preferably bacteria, or eukaryotic, preferably yeast or mammalian cells. A preferred vector system includes baculovirus expressed in insect cells. The DNA can be incorporated into host organisms by transformation, transduction, transfection, infection or related processes known in the art. In addition to DNA and mRNA sequences encoding the GP88 polypeptide, the invention also provides methods for expression of the nucleic acid sequence. Further, the genetic sequences and oligonucleotides allow identification and cloning of additional polypeptides having sequence homology to the polypeptide GP88 described here.

An expression vector is a vector which (due to the presence of appropriate transcriptional and/or translational control sequences) is capable of expressing a DNA (or cDNA) molecule which has been cloned into the vector and thereby produces a polypeptide or protein. Expression of the cloned sequence occurs when the expression vector is introduced into an appropriate host cell. If a prokaryotic expression vector is employed, then the appropriate host cell would be any prokaryotic cell capable of expressing the cloned sequence. Similarly, if an eukaryotic expression system is employed, then the appropriate host cell would be any eukaryotic cell capable of expressing the cloned sequence.

Baculovirus vector, for example, can be used to clone GP88 cDNA and subsequently express the cDNA in insect cells.

A DNA sequence encoding GP88 polypeptide or its functional derivatives may be recombined with vector DNA in accordance with conventional techniques including blunt-ended or staggered ended termini for ligation, restriction enzyme digestion to provide appropriate termini, filling in cohesive ends as appropriate, alkaline phosphatase treatment to avoid undesirable joining, and ligation with proper enzyme ligases. Techniques for such manipulations are discussed in (35).

A nucleic acid molecule is capable of expressing a polypeptide if it contains nucleotide sequences which contain transcriptional and translational regulatory information and such sequences are operably linked to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary from organism to organism but shall in general include a promoter region, which in prokaryotes contains both the promoter (which directs the initiation of RNA transcription) as well as the DNA sequences which when transcribed into RNA will signal the initiation of protein synthesis. Such regions will normally include those 5' non-coding sequences involved with the initiation of transcription, translation such as the TATA box, capping sequence, CAAT sequence and the like.

If desired, the 3' non-coding region to the gene sequence encoding the protein may be obtained by described methods (screening appropriate cDNA library or PCR amplification). This region may be retained for the presence of transcriptional termination regulatory sequences such as termination and polyadenylation. Thus, by retaining the 3' region naturally contiguous to the DNA sequence coding for the protein, the transcriptional termination signals may be provided. Where the transcription termination signals are not provided or satisfactorily functional in the expression host cells, then a 3' region from another gene may be substituted.

Two DNA sequences such as a promoter region sequence and GP88 encoding sequence are said to be operably linked if the nature of the linkage between the sequences does not result in the introduction of a frame-shift mutation or interfere with the ability of the promoter sequence to direct transcription of the polypeptide gene sequence. The promoter sequences may be prokaryotic, eukaryotic or viral. Suitable promoters are inducible, repressible or constitutive.

Eukaryotic promoters include, but are not limited to, the promoter for the mouse methallothionein I gene, the TK promoter of Herpes Virus, the gene gal4 promoter, the SV40 early promoter, the mouse mammary tumor virus (MMTV) promoter, and the cytomegalovirus (CMV) promoter. Strong promoters are preferred. Examples of such promoters are those which recognize the T3, SP6 and T7 polymerases, the PL promoter of bacteriophage lambda, the recA promoter, the promoter of the mouse methallothionein I gene, the SV40 promoter and the CMV promoter.

It is to be understood that application of the teachings of the present invention to a specific problem or environment will be within the capability of one having ordinary skill in the art in light of the teachings contained herein. The present invention is more fully illustrated by the following non-limiting examples.

EXAMPLE 1

GP88 Antagonists Induce Apoptosis In Tamoxifen-Treated Cells

GP88 overexpression blocks down-regulation of Bcl-2 mRNA transcript in response to tamoxifen treatment. MCF-7 cells and MCF-7 cells overexpressing GP88 (O4 cells) were treated with 0 to 2 µm tamoxifen. FIG. 6. 5 µg of total RNA was reverse transcribed into single strand cDNA by Super Script II (BRL, Gaithersburg, Md.) using 20 ng random hexamer (Gibco) as primer. The reverse transcription reaction was carried out for 1 h at 42 C in 10 nM Tris-HCl (pH8.3), 2.5 mM $MgCl_2$, 50 mM KCl, DTT 0.01 M and dNTP (each 0.5 mM). A total of 30-35 PCR cycles depending on the gene amplified were performed, followed by electrophoresis on 1% agarose gel. The specific primer pairs used were as follows: for glyceraldehyde 3-phosphate dehydrogenase (GAPDH): forward primer 5' TGAAG-GTCGGAGTCAACGGATTTGGT 3' (SEQ ID NO: 9), reverse primer, 5' CATGTGGGCCATGAGGTCCACCAC 3' (SEQ ID NO: 10); for Bcl-2: forward primer 5' GGTGC-CACCTGTGGTCCACCTG 3' (SEQ ID NO: 11), reverse primer 5' CTTCACTTGTGGCCCAGATAGG 3' (SEQ ID NO: 12); for Bax: forward primer 5' GAGCAGATCAT-GAAGACAGGGG 3' (SEQ ID NO: 13), reverse primer 5' CTCCAGCAAGGCCCAGCGTC 3' (SEQ ID NO: 14); for Bcl-xl: forward primer 5' CAGTGAGTGAGCAGGT-GTTTTGG 3' (SEQ ID NO: 15), reverse primer 5' GTTC-CACAAAAGTATCCCAGCCG 3' (SEQ ID NO: 16).

As shown in FIG. 6, Bcl-2 was down-regulated in cells treated with tamoxifen that do not overexpress GP88 (lanes 1-4-empty vector). Bcl-2 down-regulation was blocked in cells overexpressing GP88 and treated with tamoxifen (lanes 5-8).

EXAMPLE 2

Anti-GP88 Antibody 5B4 Induces Apoptosis in Cells Overexpressing GP88 (O4 Cells) or Cells Resistant to Tamoxifen As discussed above, cleavage of PARP releases an 85 kDa fragment indicating the cell is undergoing apoptosis. Western blot analysis using an anti-PARP antibody revealed the presence or absence of apoptosis in cells treated with combinations of tamoxifen, anti-GP88 antibody, and estradiol.

MCF-7 cells or O4 cells were seeded at a density of $7 \times 10^5$ cells in 60-mm dish in DMEM/F12 supplemented with 5% FBS. After 24 hours, medium was changed to serum-free phenol red-free DMEM/F12 supplemented with vehicle or purified GP88. After another 24 hours, cells were treated with either vehicle only or various combinations of tamoxifen, anti-GP88 antibody, estradiol, or vehicle for 24 hours. Cell lysates were collected in 6M urea in RIPA buffer (50 mM Tris HCl pH 7.4, 1% NP-40, 0.25% sodium deoxycholate, 150 mM NaCl, 1 mM EDTA, 1 mM sodium orthovanadate, 1 mM NaF, protease inhibitors). 100 µg of protein from each sample was used for immunoblotting with anti-PARP antibody. Intact and cleaved forms of PARP were detected using a mouse monoclonal anti-PARP antibody from Oncogene Research (San Diego, Calif.). α-Actin was used for normalizing the loading.

As shown in FIG. 5, GP88 inhibits induction of apoptosis by tamoxifen. Estradiol, an activator of the estrogen receptor pathway, also blocks induction of apoptosis by tamoxifen.

FIGS. 21 and 22 show that anti-GP88 antibody 5B4 induces apoptosis in cells overexpressing GP88 (O4 cells) or cells resistant to tamoxifen.

The above description and examples are only illustrative of embodiments which achieve the objects, features, and advantages of the present invention, and it is not intended that the present invention be limited thereto. Any modifications of the present invention which come within the spirit and scope of the following claims is considered part of the present invention.

---

What is claimed as new and desired to be protected by Letters Patent of the United States is:

1. A method for restoring sensitivity to antitumorigenic effects of antiestrogen therapy, comprising contacting a breast tumor cell that is nonsensitive to the antitumorigenic effects of antiestrogen therapy with a PCDGF antagonist in an amount effective to restore sensitivity to antitumorigenic effects of antiestrogen therapy, wherein the PCDGF antagonist is an antibody or antibody fragment thereof produced from a hybridoma cell line selected from the group consisting of 6B3 hybridoma cell line (ATCC Accession Number PTA-5262), 6B2 hybridoma cell line (ATCC Accession Number PTA-5261), 6C12 hybridoma cell line (ATCC Accession Number PTA-5597), 5B4 hybridoma cell line (ATCC Accession Number PTA-5260), 5G6 hybridoma cell line (ATCC Accession Number PTA-5595), 4D1 hybridoma cell line (ATCC Accession Number PTA-5593), 3F8 hybridoma cell line (ATCC Accession Number PTA-5591), 3F5 hybridoma cell line (ATCC Accession Number PTA-5259), 3F4 hybridoma cell line (ATCC Accession Number PTA-5590), 3G2 (ATCC Accession Number PTA-5592), and 2A5 hybridoma cell line (ATCC Accession Number PTA-5589).

2. The method of claim 1, wherein the antiestrogen therapy is selected from the group consisting of tamoxifen, raloxifene, aromatase inhibitors, and estrogen receptor down-regulators.

3. A method of inducing apoptosis in a tumor cell, comprising contacting a PCDGF antagonist to a tumor cell in an amount effective to induce apoptosis of the tumor cell, wherein the PCDGF antagonist is an antibody or antibody fragment thereof produced from a hybridoma cell line selected from the group consisting of 6B3 hybridoma cell line (ATCC Accession Number PTA-5262), 6B2 hybridoma cell line (ATCC Accession Number PTA-5261), 6C12 hybridoma cell line (ATCC Accession Number PTA-5597), 5B4 hybridoma cell line (ATCC Accession Number PTA-5260), 5G6 hybridoma cell line (ATCC Accession Number PTA-5595): 4D1 hybridoma cell line (ATCC Accession Number PTA-5593), 3F8 hybridoma cell line (ATCC Accession Number PTA-5591), 3F5 hybridoma cell line (ATCC Accession Number PTA-5259), 3F4 hybridoma cell line (ATCC Accession Number PTA-5590): 3G2 (ATCC Accession Number PTA-5592), and 2A5 hybridoma cell line (ATCC Accession Number PTA-5589).

4. The method of claim 3, wherein the tumor cell is selected from the group consisting of prostate, head and neck, neural, nasopharynx, thyroid, bladder, cervix, colorectal, blood, liver, kidney, breast, bone, pancreas, bone marrow, testes, ovaries, brain, neural, colon, and lung tumors.

5. A method of inducing apoptosis in a tumor cell, comprising contacting a PCDGF antagonist and an anti-estrogen with the tumor cell to induce apoptosis in the tumor cell~wherein the PCDGF antagonist is an antibody or antibody fragment thereof produced from a hybridoma cell line selected from the group consisting of 6B3 hybridoma cell line (ATCC Accession Number PTA-5262), 6B2 hybridoma cell line (ATCC Accession Number PTA-5261), 6C 12 hybridoma cell line (ATCC Accession Number PTA-5597), 5B4 hybridoma cell line (ATCC Accession Number PTA-5260), 5G6 hybridoma cell line (ATCC Accession Number PTA-5595), 4D1 hybridoma cell line (ATCC Accession Number PTA-5593), 3F8 hybridoma cell line (ATCC Accession Number PTA-5591), 3F5 hybridoma cell line (ATCC Accession Number PTA-5259), 3F4 hybridoma cell line (ATCC Accession Number PTA-5590), 3G2 (ATCC Accession Number PTA-5592), and 2A5 hybridoma cell line (ATCC Accession Number PTA-5589).

6. The method of claim 5, wherein the anti-estrogen is selected from group consisting of tamoxifen, raloxifene, aromatase inhibitors, and estrogen receptor down-regulators.

7. The method of claim 5 wherein the tumor cell is from a tumor selected from the group consisting of prostate, head and neck, nasopharynx, cervix, colorectal, bladder, thyroid, pancreas, blood, liver, kidney, breast, bone, bone marrow, testes, ovaries, brain, neural, colon, and lung tumors.

* * * * *

SEQUENCE LISTING

<160> NUMBER OF SEQ ID NOS: 17

<210> SEQ ID NO 1
<211> LENGTH: 2137
<212> TYPE: DNA
<213> ORGANISM: Mus musculus
<220> FEATURE:
<221> NAME/KEY: CDS
<222> LOCATION: (23)..(1789)

<400> SEQUENCE: 1

```
cggaccccga cgcagacaga cc atg tgg gtc ctg atg agc tgg ctg gcc ttc        52
                         Met Trp Val Leu Met Ser Trp Leu Ala Phe
                          1               5                  10 gcg gca ggg ctg gta gcc gga aca cag tgt cca gat ggg cag ttc tgc        100
Ala Ala Gly Leu Val Ala Gly Thr Gln Cys Pro Asp Gly Gln Phe Cys
             15                  20                  25 cct gtt gcc tgc tgc ctt gac cag gga gga gcc aac tac agc tgc tgt        148
Pro Val Ala Cys Cys Leu Asp Gln Gly Gly Ala Asn Tyr Ser Cys Cys
         30                  35                  40 aac cct ctt ctg gac aca tgg cct aga ata acg agc cat cat cta gat        196
Asn Pro Leu Leu Asp Thr Trp Pro Arg Ile Thr Ser His His Leu Asp
     45                  50                  55 ggc tcc tgc cag acc cat ggc cac tgt cct gct ggc tat tct tgt ctt        244
Gly Ser Cys Gln Thr His Gly His Cys Pro Ala Gly Tyr Ser Cys Leu
 60                  65                  70 ctc act gtg tct ggg act tcc agc tgc tgc ccg ttc tct aag ggt gtg        292
Leu Thr Val Ser Gly Thr Ser Ser Cys Cys Pro Phe Ser Lys Gly Val
75                  80                  85                  90 tct tgt ggt gat ggc tac cac tgc tgc ccc cag ggc ttc cac tgt agt        340
Ser Cys Gly Asp Gly Tyr His Cys Cys Pro Gln Gly Phe His Cys Ser
                 95                 100                 105 gca gat ggg aaa tcc tgc ttc cag atg tca gat aac ccc ttg ggt gct        388
Ala Asp Gly Lys Ser Cys Phe Gln Met Ser Asp Asn Pro Leu Gly Ala
            110                 115                 120 gtc cag tgt cct ggg agc cag ttt gaa tgt cct gac tct gcc acc tgc        436
Val Gln Cys Pro Gly Ser Gln Phe Glu Cys Pro Asp Ser Ala Thr Cys
        125                 130                 135 tgc att atg gtt gat ggt tcg tgg gga tgt tgt ccc atg ccc cag gcc        484
Cys Ile Met Val Asp Gly Ser Trp Gly Cys Cys Pro Met Pro Gln Ala
    140                 145                 150 tct tgc tgt gaa gac aga gtg cat tgc tgt ccc cat ggg gcc tcc tgt        532
Ser Cys Cys Glu Asp Arg Val His Cys Cys Pro His Gly Ala Ser Cys
155                 160                 165                 170 gac ctg gtt cac aca cga tgc gtt tca ccc acg ggc acc cac acc cta        580
Asp Leu Val His Thr Arg Cys Val Ser Pro Thr Gly Thr His Thr Leu
                175                 180                 185 cta aag aag ttc cct gca caa aag acc aac agc gca gtg tct ttg cct        628
Leu Lys Lys Phe Pro Ala Gln Lys Thr Asn Ser Ala Val Ser Leu Pro
            190                 195                 200 ttt tct gtc gtg tgc cct gat gct aag acc cag tgt ccc gat gat tct        676
Phe Ser Val Val Cys Pro Asp Ala Lys Thr Gln Cys Pro Asp Asp Ser
        205                 210                 215 acc tgc tgt gag cta ccc act ggg aag tat ggc tgc tgt cca atg ccc        724
```

```
            Thr Cys Cys Glu Leu Pro Thr Gly Lys Tyr Gly Cys Cys Pro Met Pro
                220                 225                 230 aat gcc atc tgc tgt tcc gac cac ctg cac tgc tgc ccc cag gac act        772
Asn Ala Ile Cys Cys Ser Asp His Leu His Cys Cys Pro Gln Asp Thr
235                 240                 245                 250 gta tgt gac ctg atc cag agt aag tgc cta tcc aag aac tac acc acg        820
Val Cys Asp Leu Ile Gln Ser Lys Cys Leu Ser Lys Asn Tyr Thr Thr
                255                 260                 265 gat ctc ctg acc aag ctg cct gga tac cca gtg aag gag gtg aag tgc        868
Asp Leu Leu Thr Lys Leu Pro Gly Tyr Pro Val Lys Glu Val Lys Cys
            270                 275                 280 gac atg gag gtg agc tgc cct gaa gga tat acc tgc tgc cgc ctc aac        916
Asp Met Glu Val Ser Cys Pro Glu Gly Tyr Thr Cys Cys Arg Leu Asn
        285                 290                 295 act ggg gcc tgg ggc tgc tgt cca ttt gcc aag gcc gtg tgt tgt gac        964
Thr Gly Ala Trp Gly Cys Cys Pro Phe Ala Lys Ala Val Cys Cys Asp
    300                 305                 310 gat cac att cat tgc tgc ccg gca ggg ttt cag tgt cac aca gag aaa       1012
Asp His Ile His Cys Cys Pro Ala Gly Phe Gln Cys His Thr Glu Lys
315                 320                 325                 330 gga acc tgc gaa atg ggt atc ctc caa gta ggg tgg atg aag aag gtc       1060
Gly Thr Cys Glu Met Gly Ile Leu Gln Val Gly Trp Met Lys Lys Val
                335                 340                 345 ata gcc ccc ctc cgc ctg cca gac cca cag atc ttg aag agt gat aca       1108
Ile Ala Pro Leu Arg Leu Pro Asp Pro Gln Ile Leu Lys Ser Asp Thr
            350                 355                 360 cct tgt gat gac ttc act agg tgt cct aca aac aat acc tgc tgc aaa       1156
Pro Cys Asp Asp Phe Thr Arg Cys Pro Thr Asn Asn Thr Cys Cys Lys
        365                 370                 375 ctc aat tct ggg gac tgg ggc tgc tgt ccc atc cca gag gct gtc tgc       1204
Leu Asn Ser Gly Asp Trp Gly Cys Cys Pro Ile Pro Glu Ala Val Cys
    380                 385                 390 tgc tca gac aac cag cat tgc tgc cct cag ggc ttc aca tgt ctg gct       1252
Cys Ser Asp Asn Gln His Cys Cys Pro Gln Gly Phe Thr Cys Leu Ala
395                 400                 405                 410 cag ggg tac tgt cag aag gga gac aca atg gtg gct ggc ctg gag aag       1300
Gln Gly Tyr Cys Gln Lys Gly Asp Thr Met Val Ala Gly Leu Glu Lys
                415                 420                 425 ata cct gcc cgc cag aca acc ccg ctc caa att gga gat atc ggt tgt       1348
Ile Pro Ala Arg Gln Thr Thr Pro Leu Gln Ile Gly Asp Ile Gly Cys
            430                 435                 440 gac cag cat acc agc tgc cca gta ggg caa acc tgc tgc cca agc ctc       1396
Asp Gln His Thr Ser Cys Pro Val Gly Gln Thr Cys Cys Pro Ser Leu
        445                 450                 455 aag gga agt tgg gcc tgc tgc cag ctg ccc cat gct gtg tgc tgt gag       1444
Lys Gly Ser Trp Ala Cys Cys Gln Leu Pro His Ala Val Cys Cys Glu
    460                 465                 470 gac cgg cag cac tgt tgc ccg gcc ggg tac acc tgc aac gtg aag gcg       1492
Asp Arg Gln His Cys Cys Pro Ala Gly Tyr Thr Cys Asn Val Lys Ala
475                 480                 485                 490 agg acc tgt gag aag gat gtc gat ttt atc cag cct ccc gtg ctc ctg       1540
Arg Thr Cys Glu Lys Asp Val Asp Phe Ile Gln Pro Pro Val Leu Leu
                495                 500                 505 acc ctc ggc cct aag gtt ggg aat gtg gag tgt gga gaa ggg cat ttc       1588
Thr Leu Gly Pro Lys Val Gly Asn Val Glu Cys Gly Glu Gly His Phe
            510                 515                 520 tgc cat gat aac cag acc tgt tgt aaa gac agt gca gga gtc tgg gcc       1636
Cys His Asp Asn Gln Thr Cys Cys Lys Asp Ser Ala Gly Val Trp Ala
        525                 530                 535
```

```
                                              -continued tgc tgt ccc tac cta aag ggt gtc tgc tgt aga gat gga cgt cac tgt    1684
Cys Cys Pro Tyr Leu Lys Gly Val Cys Cys Arg Asp Gly Arg His Cys
540                 545                 550 tgc ccc ggt ggc ttc cac tgt tca gcc agg gga acc aag tgt ttg cga    1732
Cys Pro Gly Gly Phe His Cys Ser Ala Arg Gly Thr Lys Cys Leu Arg
555                 560                 565                 570 aag aag att cct cgc tgg gac atg ttt ttg agg gat ccg gtc cca aga    1780
Lys Lys Ile Pro Arg Trp Asp Met Phe Leu Arg Asp Pro Val Pro Arg
                575                 580                 585 ccg cta ctg taaggaaggg ctacagactt aaggaactcc acagtcctgg            1829
Pro Leu Leu gaaccctgtt ccgagggtac ccactactca ggcctcccta gcgcctcctc ccctaacgtc  1889
tccccggcct actcatcctg agtcacccta tcaccatggg aggtggagcc tcaaactaaa  1949
accttctttt atggaaagaa ggctctggcc aaaagccccg tatcaaactg ccatttcttc  2009
cggtttctgt ggaccttgtg gccaggtgct cttcccgagc acaggtgtt ctgtgagctt   2069 gcttgtgtgt gtgtgcgcgt gtgcgtgtgt tgctccaata agtttgtac gctttctgaa   2129 aaaaaaaa                                                           2137

<210> SEQ ID NO 2
<211> LENGTH: 589
<212> TYPE: PRT
<213> ORGANISM: Mus musculus

<400> SEQUENCE: 2

Met Trp Val Leu Met Ser Trp Leu Ala Phe Ala Ala Gly Leu Val Ala
 1               5                  10                  15

Gly Thr Gln Cys Pro Asp Gly Gln Phe Cys Pro Val Ala Cys Cys Leu
                20                  25                  30

Asp Gln Gly Gly Ala Asn Tyr Ser Cys Cys Asn Pro Leu Leu Asp Thr
            35                  40                  45

Trp Pro Arg Ile Thr Ser His Leu Asp Gly Ser Cys Gln Thr His
        50                  55                  60

Gly His Cys Pro Ala Gly Tyr Ser Cys Leu Leu Thr Val Ser Gly Thr
 65                  70                  75                  80

Ser Ser Cys Cys Pro Phe Ser Lys Gly Val Ser Cys Gly Asp Gly Tyr
                 85                  90                  95

His Cys Cys Pro Gln Gly Phe His Cys Ser Ala Asp Gly Lys Ser Cys
                100                 105                 110

Phe Gln Met Ser Asp Asn Pro Leu Gly Ala Val Gln Cys Pro Gly Ser
            115                 120                 125

Gln Phe Glu Cys Pro Asp Ser Ala Thr Cys Cys Ile Met Val Asp Gly
        130                 135                 140

Ser Trp Gly Cys Cys Pro Met Pro Gln Ala Ser Cys Cys Glu Asp Arg
145                 150                 155                 160

Val His Cys Cys Pro His Gly Ala Ser Cys Asp Leu Val His Thr Arg
                165                 170                 175

Cys Val Ser Pro Thr Gly Thr His Thr Leu Leu Lys Lys Phe Pro Ala
                180                 185                 190

Gln Lys Thr Asn Ser Ala Val Ser Leu Pro Phe Ser Val Val Cys Pro
            195                 200                 205

Asp Ala Lys Thr Gln Cys Pro Asp Ser Thr Cys Cys Glu Leu Pro
        210                 215                 220

Thr Gly Lys Tyr Gly Cys Cys Pro Met Pro Asn Ala Ile Cys Cys Ser
225                 230                 235                 240
```

```
Asp His Leu His Cys Cys Pro Gln Asp Thr Val Cys Asp Leu Ile Gln
                245                 250                 255
Ser Lys Cys Leu Ser Lys Asn Tyr Thr Thr Asp Leu Leu Thr Lys Leu
            260                 265                 270
Pro Gly Tyr Pro Val Lys Glu Val Lys Cys Asp Met Glu Val Ser Cys
        275                 280                 285
Pro Glu Gly Tyr Thr Cys Cys Arg Leu Asn Thr Gly Ala Trp Gly Cys
    290                 295                 300
Cys Pro Phe Ala Lys Ala Val Cys Cys Asp Asp His Ile His Cys Cys
305                 310                 315                 320
Pro Ala Gly Phe Gln Cys His Thr Glu Lys Gly Thr Cys Glu Met Gly
                325                 330                 335
Ile Leu Gln Val Gly Trp Met Lys Lys Val Ile Ala Pro Leu Arg Leu
            340                 345                 350
Pro Asp Pro Gln Ile Leu Lys Ser Asp Thr Pro Cys Asp Asp Phe Thr
        355                 360                 365
Arg Cys Pro Thr Asn Asn Thr Cys Cys Lys Leu Asn Ser Gly Asp Trp
    370                 375                 380
Gly Cys Cys Pro Ile Pro Glu Ala Val Cys Cys Ser Asp Asn Gln His
385                 390                 395                 400
Cys Cys Pro Gln Gly Phe Thr Cys Leu Ala Gln Gly Tyr Cys Gln Lys
                405                 410                 415
Gly Asp Thr Met Val Ala Gly Leu Glu Lys Ile Pro Ala Arg Gln Thr
            420                 425                 430
Thr Pro Leu Gln Ile Gly Asp Ile Gly Cys Asp Gln His Thr Ser Cys
        435                 440                 445
Pro Val Gly Gln Thr Cys Cys Pro Ser Leu Lys Gly Ser Trp Ala Cys
    450                 455                 460
Cys Gln Leu Pro His Ala Val Cys Cys Glu Asp Arg Gln His Cys Cys
465                 470                 475                 480
Pro Ala Gly Tyr Thr Cys Asn Val Lys Ala Arg Thr Cys Glu Lys Asp
                485                 490                 495
Val Asp Phe Ile Gln Pro Pro Val Leu Leu Thr Leu Gly Pro Lys Val
            500                 505                 510
Gly Asn Val Glu Cys Gly Glu Gly His Phe Cys His Asp Asn Gln Thr
        515                 520                 525
Cys Cys Lys Asp Ser Ala Gly Val Trp Ala Cys Cys Pro Tyr Leu Lys
    530                 535                 540
Gly Val Cys Cys Arg Asp Gly Arg His Cys Cys Pro Gly Gly Phe His
545                 550                 555                 560
Cys Ser Ala Arg Gly Thr Lys Cys Leu Arg Lys Lys Ile Pro Arg Trp
                565                 570                 575
Asp Met Phe Leu Arg Asp Pro Val Pro Arg Pro Leu Leu
            580                 585

<210> SEQ ID NO 3
<211> LENGTH: 2095
<212> TYPE: DNA
<213> ORGANISM: Homo sapiens

<400> SEQUENCE: 3
cgcaggcaga ccatgtggac cctggtgagc tgggtggcct taacagcagg gctggtggct      60
ggaacgcggt gcccagatgg tcagttctgc cctgtggcct gctgcctgga ccccggagga     120
```

```
gccagctaca gctgctgccg tccccttctg gacaaatggc ccacaacact gagcaggcat    180
ctgggtggcc cctgccaggt tgatgccac tgctctgccg gccactcctg catctttacc    240
gtctcaggga cttccagttg ctgcccttc ccagaggccg tggcatgcgg ggatggccat    300
cactgctgcc cacggggctt ccactgcagt gcagacgggc gatcctgctt ccaaagatca    360
ggtaacaact ccgtgggtgc catccagtgc cctgatagtc agttcgaatg cccggacttc    420
tccacgtgct gtgttatggt cgatggctcc tgggggtgct gccccatgcc ccaggcttcc    480
tgctgtgaag acagggtgca ctgctgtccg cacggtgcct tctgcgacct ggttcacacc    540
cgctgcatca cacccacggg caccacccc ctggcaaaga agctccctgc cagaggact    600 aacagggcag tggccttgtc agctcggtc atgtgtccgg acgcacggtc ccggtgccct    660
gatggttcta cctgctgtga gctgccagt gggaagtatg gctgctgccc aatgccaac    720 gccacctgct gctccgatca cctgcactgc tgccccaag acactgtgtg tgacctgatc    780
cagagtaagt gcctctccaa ggagaacgct accacgacc tcctcactaa gctgcctgcg    840
cacacagtgg gcgatgtgaa atgtgacatg gaggtgagct gcccagatgg ctatacctgc    900
tgccgtctac agtcggggc tgggctgc tgccctttta cccaggctgt gtgctgtgag    960
gaccacatac actgctgtcc cgcggggttt acgtgtgaca cgcagaaggg tacctgtgaa    1020
caggggcccc accaggtgcc ctggatggag aaggcccag ctcacctcag cctgccagac    1080
ccacaagcct tgaagagaga gtccccctgt gataatgtca gcagctgtcc ctcctccgat    1140
acctgctgcc aactcacgtc tggggagtgg gctgctgtc caatcccaga ggctgtctgc    1200
tgctcggacc accagcactg ctgccccag cgatacacgt gtgtagctga ggggcagtgt    1260
cagcgaggaa gcgagatcgt ggctggactg gagaagatgc ctgcccgccg cggttccta    1320 tcccacccca gagacatcgg ctgtgaccag cacaccagct gcccggtggg cggaacctgc    1380
tgcccgagcc agggtgggag ctgggcctgc tgccagttgc cccatgctgt gtgctgcgag    1440
gatcgccagc actgctgccc ggctggctac acctgcaacg tgaaggctcg atcctgcgag    1500
aaggaagtgg tctctgccca gcctgccacc ttcctggccc gtagccctca cgtgggtgtg    1560
aaggacgtgg agtgtgggga aggacacttc tgccatgata ccagacctg ctgccgagac    1620 aaccgacagg gctgggcctg ctgtcctac gcccagggcg tctgttgtgc tgatcggcgc    1680
cactgctgtc ctgctggctt ccgctgcgca cgcagggta ccaagtgttt gcgcagggag    1740
gccccgcgct gggacgcccc tttgaggac ccagccttga cagctgct gtgagggaca    1800 gtactgaaga ctctgcagcc ctcgggaccc cactcggagg gtgccctctg ctcaggcctc    1860
cctagcacct cccctaacc aaattctccc tggaccccat tctgagctcc ccatcaccat    1920
gggaggtggg gcctcaatct aaggcccttc cctgtcagaa gggggttgag gcaaaagccc    1980
attacaagct gccatcccct ccccgttca gtggaccctg tggccaggtg ctttcccta    2040 tccacagggg tgtttgtgtg ttgggtgtgc tttcaataaa gtttgtcact ttctt    2095
```

<210> SEQ ID NO 4
<211> LENGTH: 1676
<212> TYPE: PRT
<213> ORGANISM: Homo sapiens

<400> SEQUENCE: 4

Met Glu Thr Thr Arg Pro Thr His Arg Leu Glu Val Ala Leu Ser Glu
1               5                   10                  15

Arg Thr Arg Pro Val Ala Leu Ala Leu Ala Leu Glu Thr His Arg Ala
            20                  25                  30

-continued

```
Leu Ala Gly Leu Tyr Leu Glu Val Ala Leu Ala Leu Ala Gly Leu Tyr
        35                  40                  45

Thr His Arg Ala Arg Gly Cys Tyr Ser Pro Arg Ala Ser Pro Gly Leu
    50                  55                  60

Tyr Gly Leu Asn Pro His Glu Cys Tyr Ser Pro Arg Val Ala Leu Ala
65                  70                  75                  80

Leu Ala Cys Tyr Ser Cys Tyr Ser Leu Glu Ala Ser Pro Pro Arg Gly
                85                  90                  95

Leu Tyr Gly Leu Tyr Ala Leu Ala Ser Glu Arg Thr Tyr Arg Ser Glu
            100                 105                 110

Arg Cys Tyr Ser Cys Tyr Ser Ala Arg Gly Pro Arg Leu Glu Leu Glu
        115                 120                 125

Ala Ser Pro Leu Tyr Ser Thr Arg Pro Pro Arg Thr His Arg Thr His
    130                 135                 140

Arg Leu Glu Ser Glu Arg Ala Arg Gly His Ile Ser Leu Glu Gly Leu
145                 150                 155                 160

Tyr Gly Leu Tyr Pro Arg Cys Tyr Ser Gly Leu Asn Val Ala Leu Ala
                165                 170                 175

Ser Pro Ala Leu Ala His Ile Ser Cys Tyr Ser Ser Glu Arg Ala Leu
            180                 185                 190

Ala Gly Leu Tyr His Ile Ser Ser Glu Arg Cys Tyr Ser Ile Leu Glu
        195                 200                 205

Pro His Glu Thr His Arg Val Ala Leu Ser Glu Arg Gly Leu Tyr Thr
    210                 215                 220

His Arg Ser Glu Arg Ser Glu Arg Cys Tyr Ser Cys Tyr Ser Pro Arg
225                 230                 235                 240

Pro His Glu Pro Arg Gly Leu Ala Leu Ala Val Ala Leu Ala Leu Ala
                245                 250                 255

Cys Tyr Ser Gly Leu Tyr Ala Ser Pro Gly Leu Tyr His Ile Ser His
            260                 265                 270

Ile Ser Cys Tyr Ser Cys Tyr Ser Pro Arg Ala Arg Gly Gly Leu Tyr
        275                 280                 285

Pro His Glu His Ile Ser Cys Tyr Ser Ser Glu Arg Ala Leu Ala Ala
    290                 295                 300

Ser Pro Gly Leu Tyr Ala Arg Gly Ser Glu Arg Cys Tyr Ser Pro His
305                 310                 315                 320

Glu Gly Leu Asn Ala Arg Gly Ser Glu Arg Gly Leu Tyr Ala Ser Asn
                325                 330                 335

Ala Ser Asn Ser Glu Arg Val Ala Leu Gly Leu Tyr Ala Leu Ala Ile
            340                 345                 350

Leu Glu Gly Leu Asn Cys Tyr Ser Pro Arg Ala Ser Pro Ser Glu Arg
        355                 360                 365

Gly Leu Asn Pro His Glu Gly Leu Cys Tyr Ser Pro Arg Ala Ser Pro
    370                 375                 380

Pro His Glu Ser Glu Arg Thr His Arg Cys Tyr Ser Cys Tyr Ser Val
385                 390                 395                 400

Ala Leu Met Glu Thr Val Ala Leu Ala Ser Pro Gly Leu Tyr Ser Glu
                405                 410                 415

Arg Thr Arg Pro Gly Leu Tyr Cys Tyr Ser Cys Tyr Ser Pro Arg Met
            420                 425                 430

Glu Thr Pro Arg Gly Leu Asn Ala Leu Ala Ser Glu Arg Cys Tyr Ser
        435                 440                 445
```

-continued

```
Cys Tyr Ser Gly Leu Ala Ser Pro Ala Arg Gly Val Ala Leu His Ile
450                 455                 460

Ser Cys Tyr Ser Cys Tyr Ser Pro Arg His Ile Ser Gly Leu Tyr Ala
465                 470                 475                 480

Leu Ala Pro His Glu Cys Tyr Ser Ala Ser Pro Leu Glu Val Ala Leu
                485                 490                 495

His Ile Ser Thr His Arg Ala Arg Gly Cys Tyr Ser Ile Leu Glu Thr
                500                 505                 510

His Arg Pro Arg Thr His Arg Gly Leu Tyr Thr His Arg His Ile Ser
            515                 520                 525

Pro Arg Leu Glu Ala Leu Ala Leu Tyr Ser Leu Tyr Ser Leu Glu Pro
            530                 535                 540

Arg Ala Leu Ala Gly Leu Asn Ala Arg Gly Thr His Arg Ala Ser Asn
545                 550                 555                 560

Ala Arg Gly Ala Leu Ala Val Ala Leu Ala Leu Ala Leu Glu Ser Glu
                565                 570                 575

Arg Ser Glu Arg Ser Glu Arg Val Ala Leu Met Glu Thr Cys Tyr Ser
            580                 585                 590

Pro Arg Ala Ser Pro Ala Leu Ala Ala Arg Gly Ser Glu Arg Ala Arg
            595                 600                 605

Gly Cys Tyr Ser Pro Arg Ala Ser Pro Gly Leu Tyr Ser Glu Arg Thr
610                 615                 620

His Arg Cys Tyr Ser Cys Tyr Ser Gly Leu Leu Glu Pro Arg Ser Glu
625                 630                 635                 640

Arg Gly Leu Tyr Leu Tyr Ser Thr Tyr Arg Gly Leu Tyr Cys Tyr Ser
                645                 650                 655

Cys Tyr Ser Pro Arg Met Glu Thr Pro Arg Ala Ser Asn Ala Leu Ala
            660                 665                 670

Thr His Arg Cys Tyr Ser Cys Tyr Ser Ser Glu Arg Ala Ser Pro His
            675                 680                 685

Ile Ser Leu Glu His Ile Ser Cys Tyr Ser Cys Tyr Ser Pro Arg Gly
690                 695                 700

Leu Asn Ala Ser Pro Thr His Arg Val Ala Leu Cys Tyr Ser Ala Ser
705                 710                 715                 720

Pro Leu Glu Ile Leu Glu Gly Leu Asn Ser Glu Arg Leu Tyr Ser Cys
                725                 730                 735

Tyr Ser Leu Glu Ser Glu Arg Leu Tyr Ser Gly Leu Ala Ser Asn Ala
            740                 745                 750

Leu Ala Thr His Arg Thr His Arg Ala Ser Pro Leu Glu Leu Glu Thr
            755                 760                 765

His Arg Leu Tyr Ser Leu Glu Pro Arg Ala Leu Ala His Ile Ser Thr
770                 775                 780

His Arg Val Ala Leu Gly Leu Tyr Ala Ser Pro Val Ala Leu Leu Tyr
785                 790                 795                 800

Ser Cys Tyr Ser Ala Ser Pro Met Glu Thr Gly Leu Val Ala Leu Ser
                805                 810                 815

Glu Arg Cys Tyr Ser Pro Arg Ala Ser Pro Gly Leu Tyr Thr Tyr Arg
            820                 825                 830

Thr His Arg Cys Tyr Ser Cys Tyr Ser Ala Arg Gly Leu Glu Gly Leu
            835                 840                 845

Asn Ser Glu Arg Gly Leu Tyr Ala Leu Ala Thr Arg Pro Gly Leu Tyr
850                 855                 860

Cys Tyr Ser Cys Tyr Ser Pro Arg Pro His Glu Thr His Arg Gly Leu
```

-continued

```
              865                 870                 875                 880
Asn Ala Leu Ala Val Ala Leu Cys Tyr Ser Cys Tyr Ser Gly Leu Ala
                885                 890                 895

Ser Pro His Ile Ser Ile Leu Glu His Ile Ser Cys Tyr Ser Cys Tyr
                900                 905                 910

Ser Pro Arg Ala Leu Ala Gly Leu Tyr Pro His Glu Thr His Arg Cys
                915                 920                 925

Tyr Ser Ala Ser Pro Thr His Arg Gly Leu Asn Leu Tyr Ser Gly Leu
                930                 935                 940

Tyr Thr His Arg Cys Tyr Ser Gly Leu Gly Leu Asn Gly Leu Tyr Pro
945                 950                 955                 960

Arg His Ile Ser Gly Leu Asn Val Ala Leu Pro Arg Thr Arg Pro Met
                965                 970                 975

Glu Thr Gly Leu Leu Tyr Ser Ala Leu Ala Pro Arg Ala Leu Ala His
                980                 985                 990

Ile Ser Leu Glu Ser Glu Arg Leu Glu Pro Arg Ala Ser Pro Pro Arg
                995                 1000                1005

Gly Leu Asn Ala Leu Ala Leu Glu Leu Tyr Ser Ala Arg Gly Ala Ser
                1010                1015                1020

Pro Val Ala Leu Pro Arg Cys Tyr Ser Ala Ser Pro Ala Ser Asn Val
1025                1030                1035                1040

Ala Leu Ser Glu Arg Ser Glu Arg Cys Tyr Ser Pro Arg Ser Glu Arg
                1045                1050                1055

Ser Glu Arg Ala Ser Pro Thr His Arg Cys Tyr Ser Cys Tyr Ser Gly
                1060                1065                1070

Leu Asn Leu Glu Thr His Arg Ser Glu Arg Gly Leu Tyr Gly Leu Thr
                1075                1080                1085

Arg Pro Gly Leu Tyr Cys Tyr Ser Cys Tyr Ser Pro Arg Ile Leu Glu
                1090                1095                1100

Pro Arg Gly Leu Ala Leu Ala Val Ala Leu Cys Tyr Ser Cys Tyr Ser
1105                1110                1115                1120

Ser Glu Arg Ala Ser Pro His Ile Ser Gly Leu Asn His Ile Ser Cys
                1125                1130                1135

Tyr Ser Cys Tyr Ser Pro Arg Gly Leu Asn Ala Arg Gly Thr Tyr Arg
                1140                1145                1150

Thr His Arg Cys Tyr Ser Val Ala Leu Ala Leu Ala Gly Leu Gly Leu
                1155                1160                1165

Tyr Gly Leu Asn Cys Tyr Ser Gly Leu Asn Ala Arg Gly Gly Leu Tyr
                1170                1175                1180

Ser Glu Arg Gly Leu Ile Leu Glu Val Ala Leu Ala Leu Ala Gly Leu
1185                1190                1195                1200

Tyr Leu Glu Gly Leu Leu Tyr Ser Met Glu Thr Pro Arg Ala Leu Ala
                1205                1210                1215

Ala Arg Gly Ala Arg Gly Gly Leu Tyr Ser Glu Arg Leu Glu Ser Glu
                1220                1225                1230

Arg His Ile Ser Pro Arg Ala Arg Gly Ala Ser Pro Ile Leu Glu Gly
                1235                1240                1245

Leu Tyr Cys Tyr Ser Ala Ser Pro Gly Leu Asn His Ile Ser Thr His
                1250                1255                1260

Arg Ser Glu Arg Cys Tyr Ser Pro Arg Val Ala Leu Gly Leu Tyr Gly
1265                1270                1275                1280

Leu Tyr Thr His Arg Cys Tyr Ser Cys Tyr Ser Pro Arg Ser Glu Arg
                1285                1290                1295
```

```
Gly Leu Asn Gly Leu Tyr Gly Leu Tyr Ser Glu Arg Thr Arg Pro Ala
            1300                1305                1310
Leu Ala Cys Tyr Ser Cys Tyr Ser Gly Leu Asn Leu Glu Pro Arg His
        1315                1320                1325
Ile Ser Ala Leu Ala Val Ala Leu Cys Tyr Ser Cys Tyr Ser Gly Leu
    1330                1335                1340
Ala Ser Pro Ala Arg Gly Gly Leu Asn His Ile Ser Cys Tyr Ser Cys
1345                1350                1355                1360
Tyr Ser Pro Arg Ala Leu Ala Gly Leu Tyr Thr Tyr Arg Thr His Arg
                1365                1370                1375
Cys Tyr Ser Ala Ser Asn Val Ala Leu Leu Tyr Ser Ala Leu Ala Ala
            1380                1385                1390
Arg Gly Ser Glu Arg Cys Tyr Ser Gly Leu Leu Tyr Ser Gly Leu Val
        1395                1400                1405
Ala Leu Val Ala Leu Ser Glu Arg Ala Leu Ala Gly Leu Asn Pro Arg
    1410                1415                1420
Ala Leu Ala Thr His Arg Pro His Glu Leu Glu Ala Leu Ala Ala Arg
1425                1430                1435                1440
Gly Ser Glu Arg Pro Arg His Ile Ser Val Ala Leu Gly Leu Tyr Val
                1445                1450                1455
Ala Leu Leu Tyr Ser Ala Ser Pro Val Ala Leu Gly Leu Cys Tyr Ser
            1460                1465                1470
Gly Leu Tyr Gly Leu Gly Leu Tyr His Ile Ser Pro His Glu Cys Tyr
        1475                1480                1485
Ser His Ile Ser Ala Ser Pro Ala Ser Asn Gly Leu Asn Thr His Arg
    1490                1495                1500
Cys Tyr Ser Cys Tyr Ser Ala Arg Gly Ala Ser Pro Ala Ser Asn Ala
1505                1510                1515                1520
Arg Gly Gly Leu Asn Gly Leu Tyr Thr Arg Pro Ala Leu Ala Cys Tyr
                1525                1530                1535
Ser Cys Tyr Ser Pro Arg Thr Tyr Arg Ala Leu Ala Gly Leu Asn Gly
            1540                1545                1550
Leu Tyr Val Ala Leu Cys Tyr Ser Cys Tyr Ser Ala Leu Ala Ala Ser
        1555                1560                1565
Pro Ala Arg Gly Ala Arg Gly His Ile Ser Cys Tyr Ser Cys Tyr Ser
    1570                1575                1580
Pro Arg Ala Leu Ala Gly Leu Tyr Pro His Glu Ala Arg Gly Cys Tyr
1585                1590                1595                1600
Ser Ala Leu Ala Ala Arg Gly Ala Arg Gly Gly Leu Tyr Thr His Arg
                1605                1610                1615
Leu Tyr Ser Cys Tyr Ser Leu Glu Ala Arg Gly Ala Arg Gly Gly Leu
            1620                1625                1630
Ala Leu Ala Pro Arg Ala Arg Gly Thr Arg Pro Ala Ser Pro Ala Leu
        1635                1640                1645
Ala Pro Arg Leu Glu Ala Arg Gly Ala Ser Pro Arg Ala Leu Ala
    1650                1655                1660
Leu Glu Ala Arg Gly Gly Leu Asn Leu Glu Leu Glu
1665                1670                1675

<210> SEQ ID NO 5
<211> LENGTH: 21
<212> TYPE: DNA
<213> ORGANISM: Artificial Sequence
<220> FEATURE:
```

<223> OTHER INFORMATION: Description of Artificial Sequence: Synthetic
      polynucleotide sequence

<400> SEQUENCE: 5
aggttgatgc ccactgctct g                                              21

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide sequence

<400> SEQUENCE: 6
gagcagtggg caucaaccug g                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 7
agatcaggta acaactccgt g                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 8
ggacacttct gccatgataa c                                              21

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 9
tgaaggtcgg agtcaacgga tttggt                                         26

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 10
catgtgggcc atgaggtcca ccac                                           24

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic -continued PCR primer

<400> SEQUENCE: 11
ggtgccacct gtggtccacc tg                                                22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 12
cttcacttgt ggcccagata gg                                                22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 13
gagcagatca tgaagacagg gg                                                22

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 14
ctccagcaag gcccagcgtc                                                   20

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 15
cagtgagtga gcaggtgttt tgg                                               23

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 16
gttccacaaa agtatcccag ccg                                               23

<210> SEQ ID NO 17
<211> LENGTH: 55
<212> TYPE: PRT
<213> ORGANISM: Artificial Sequence
<220> FEATURE:
<223> OTHER INFORMATION: Description of Artificial Sequence: Consensus
      sequence

```
<220> FEATURE:
<221> NAME/KEY: MOD_RES
<222> LOCATION: (2)..(7)
<223> OTHER INFORMATION: Variable amino acid
<220> FEATURE:
<221> NAME/KEY: MOD_RES
<222> LOCATION: (9)..(13)
<223> OTHER INFORMATION: Variable amino acid
<220> FEATURE:
<221> NAME/KEY: MOD_RES
<222> LOCATION: (16)..(20)
<223> OTHER INFORMATION: Variable amino acid
<220> FEATURE:
<221> NAME/KEY: MOD_RES
<222> LOCATION: (22)..(25)
<223> OTHER INFORMATION: Variable amino acid
<220> FEATURE:
<221> NAME/KEY: MOD_RES
<222> LOCATION: (28)..(33)
<223> OTHER INFORMATION: Variable amino acid
<220> FEATURE:
<221> NAME/KEY: MOD_RES
<222> LOCATION: (36)
<223> OTHER INFORMATION: Variable amino acid
<220> FEATURE:
<221> NAME/KEY: MOD_RES
<222> LOCATION: (38)..(39)
<223> OTHER INFORMATION: Variable amino acid
<220> FEATURE:
<221> NAME/KEY: MOD_RES
<222> LOCATION: (44)..(47)
<223> OTHER INFORMATION: Variable amino acid
<220> FEATURE:
<221> NAME/KEY: MOD_RES
<222> LOCATION: (49)..(54)
<223> OTHER INFORMATION: Variable amino acid

<400> SEQUENCE: 17

Cys Xaa Xaa Xaa Xaa Xaa Xaa Cys Xaa Xaa Xaa Xaa Xaa Cys Cys Xaa
 1               5                   10                  15

Xaa Xaa Xaa Xaa Gly Xaa Xaa Xaa Xaa Cys Cys Xaa Xaa Xaa Xaa Xaa
            20                  25                  30

Xaa Cys Cys Xaa Asp Xaa Xaa His Cys Cys Pro Xaa Xaa Xaa Xaa Cys
        35                  40                  45

Xaa Xaa Xaa Xaa Xaa Xaa Cys
        50                  55
```